(12) United States Patent
Limon

(10) Patent No.: US 10,588,706 B2
(45) Date of Patent: Mar. 17, 2020

(54) DEVICES, SYSTEMS, AND METHODS FOR SURGICAL INSTRUMENT REPROCESSING

(71) Applicant: INTUITIVE SURGICAL OPERATIONS, INC., Sunnyvale, CA (US)

(72) Inventor: Timothy Allen Limon, Cupertino, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 495 days.

(21) Appl. No.: 14/910,204

(22) PCT Filed: Aug. 1, 2014

(86) PCT No.: PCT/US2014/049454
§ 371 (c)(1),
(2) Date: Feb. 4, 2016

(87) PCT Pub. No.: WO2015/020906
PCT Pub. Date: Feb. 12, 2015

(65) Prior Publication Data
US 2016/0175062 A1 Jun. 23, 2016

Related U.S. Application Data

(60) Provisional application No. 61/862,252, filed on Aug. 5, 2013.

(51) Int. Cl.
*A61B 34/35* (2016.01)
*A61B 34/30* (2016.01)
(Continued)

(52) U.S. Cl.
CPC .............. *A61B 34/35* (2016.02); *A61B 34/30* (2016.02); *A61B 90/70* (2016.02); *B08B 3/04* (2013.01)

(58) Field of Classification Search
CPC ......... A61B 34/30; A61B 34/35; A61B 90/70; B08B 3/01; B08B 11/02
(Continued)

(56) References Cited

U.S. PATENT DOCUMENTS

| 4,193,818 A * | 3/1980 | Young | B08B 3/12 |
| | | | 134/1 |
| 5,505,218 A * | 4/1996 | Steinhauser | A61C 19/002 |
| | | | 134/102.1 |

(Continued)

FOREIGN PATENT DOCUMENTS

| DE | 10248460 A1 * | 4/2004 | ............... A61L 2/18 |
| WO | WO-2012148266 A1 | 11/2012 | |

OTHER PUBLICATIONS

Kraft et al. (DE10248460), Machine Translation Generated Mar. 15, 2016. (Year: 2016).*

(Continued)

*Primary Examiner* — Nadine G Norton
*Assistant Examiner* — Christopher Remavege
(74) *Attorney, Agent, or Firm* — Jones Robb, PLLC

(57) ABSTRACT

An accessory drive device includes a housing, a fluid inlet, a fluid outlet, a drive mechanism, and an output drive member. The output drive member may be driven by the drive mechanism and engage with an input drive member on a transmission mechanism of a surgical instrument. The drive mechanism may be configured to be driven by a motive force produced by fluid flowing through the housing from the inlet to the outlet, with the fluid being delivered by a fluid source of a reprocessing device. A portable, accessory drive device for a surgical instrument includes a portable housing to be removably coupled to a transmission mechanism of an instrument and a drive mechanism to drive an input drive member of the transmission mechanism. A method of reprocessing a surgical instrument includes converting a force associated with a flow of fluid for reprocessing to drive an instrument input drive member.

10 Claims, 22 Drawing Sheets

(51) Int. Cl.
*A61B 90/70* (2016.01)
*B08B 3/04* (2006.01)

(58) Field of Classification Search
USPC ...... 134/32, 116, 22.12, 137, 138, 140, 141, 134/157; 706/261; 422/28, 33; 700/261
See application file for complete search history.

(56) References Cited

U.S. PATENT DOCUMENTS

| | | | |
|---|---|---|---|
| 5,554,228 A | 9/1996 | Giordano et al. | |
| 5,921,256 A * | 7/1999 | Barin | A61B 90/70 134/104.2 |
| 6,004,509 A * | 12/1999 | Dey | A61B 90/40 134/22.12 |
| 6,120,729 A | 9/2000 | Schad | |
| 6,915,810 B2 | 7/2005 | Weber | |
| 2004/0220452 A1 | 11/2004 | Shalman | |
| 2006/0190032 A1 * | 8/2006 | Wales | A61B 17/00234 606/205 |
| 2007/0125826 A1 * | 6/2007 | Shelton, IV | A61B 17/07207 227/175.1 |
| 2009/0158539 A1 | 6/2009 | Onishi et al. | |
| 2010/0179382 A1 | 7/2010 | Shelton, Iv et al. | |
| 2015/0359599 A1 * | 12/2015 | Fagan | A61B 1/21 134/18 |

OTHER PUBLICATIONS

International Search Report and Written Opinion for Application No. PCT/US2014/049454, dated Nov. 18, 2014, 13 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

DEVICES, SYSTEMS, AND METHODS FOR SURGICAL INSTRUMENT REPROCESSING

This application is a U.S. national stage application under 35 U.S.C. § 371(c) of International Application No. PCT/US2014/049454, which claims the benefit of priority of U.S. Provisional Application No. 61/862,252, filed Aug. 5, 2013, each of which is incorporated by reference herein in its entirety.

TECHNICAL FIELD

Aspects of the present disclosure relate to devices, systems, and methods for surgical instrument reprocessing. In particular, the present disclosure relates to devices and methods for actuating surgical instruments into various configurations useful for reprocessing surgical instruments.

BACKGROUND

Remotely controlled surgical instruments (including both manual laparoscopic and computer-assisted teleoperated instruments) are often used in minimally invasive medical procedures. During medical procedures, such surgical instruments may be inserted within the body of a patient to perform medical procedures. During a medical procedure, surgical instruments may be exposed to various biomaterials, including fluids, tissues, and other materials, which can become lodged, for example, in the various components of the surgical instrument.

When it is desired to reuse a surgical instrument, or one or more components of a surgical instrument, it may be desirable to reprocess the instrument, or the one or more components of the instrument, in a manner that effectively cleans all surfaces of the instrument, including interior components capable of being exposed to the biomaterials, and enables the instrument or components thereof to be reused safely.

A technician may be tasked with manually reprocessing the instrument. For example, the technician can operate the surgical instrument, such as by manually rotating input disks of the surgical instrument, while subjecting the instrument to a fluid spray or brushing process. The manual operation of the surgical instrument causes one or more parts of the instrument, e.g., an end effector thereof, to move, thereby allowing the fluid spray and/or brush to reach different parts of the instrument for effective cleaning.

Various reprocessing systems and methods rely on flushing an interior of the instrument and spraying an exterior of the instrument using water or a water-based detergent solution. Continued improvement in such reprocessing procedures and systems is desirable to provide fewer manual steps while achieving a thorough cleaning of the instrument.

SUMMARY

Exemplary embodiments of the present disclosure may demonstrate one or more of the above-mentioned desirable features. Other features and/or advantages will become apparent from the description that follows.

In accordance with at least one exemplary embodiment, an accessory drive device for surgical instrument reprocessing comprises a housing, a fluid inlet in flow communication with the housing, a fluid outlet in flow communication with the housing, a drive mechanism disposed within the housing, and an output drive member. The output drive member may be coupled to the drive mechanism to be driven by the drive mechanism. Further, the output drive member may be configured to engage with an input drive member on a transmission mechanism of the surgical instrument. The drive mechanism may be configured to be driven by a motive force produced by fluid flowing through the housing from the inlet to the outlet, with the fluid being delivered by a fluid source of a reprocessing device.

In accordance with another exemplary embodiment, a method of reprocessing a surgical instrument comprises converting a force associated with a flow of fluid used during reprocessing of a surgical instrument to a drive force sufficient to drive an input drive member of a transmission mechanism of the surgical instrument. The method may further comprise transmitting a force from the input drive member to an actuation element coupled to a distal end component of the surgical instrument. The method may further comprise imparting motion to the distal end component based on the force transmitted to the actuation element.

In accordance with another exemplary embodiment, a portable, accessory drive device for a surgical instrument comprises a portable housing and a drive mechanism. The portable housing may be configured to be removably coupled to a transmission mechanism of a surgical instrument and to be carried with the surgical instrument when coupled thereto. The drive mechanism may be disposed in the housing. The drive mechanism may comprise an output drive member configured to drive an input drive member of the transmission mechanism in a coupled state of the housing and the transmission mechanism. The drive mechanism may be configured to produce an output force at the output drive member, with the output force being sufficient to drive the input drive member to impart motion to a distal end component of a surgical instrument.

In accordance with another exemplary embodiment, a method of reprocessing a surgical instrument comprises using a first portion of a flow of fluid provided to a reprocessing unit to generate a drive force at an input drive member of a transmission mechanism of the surgical instrument and to move a distal end component of the surgical instrument responsive to the generated drive force. The method may further comprise flowing a second portion of the flow of fluid over one or more external surfaces of the surgical instrument within the reprocessing unit.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation.

DETAILED DESCRIPTION

Figure 1:
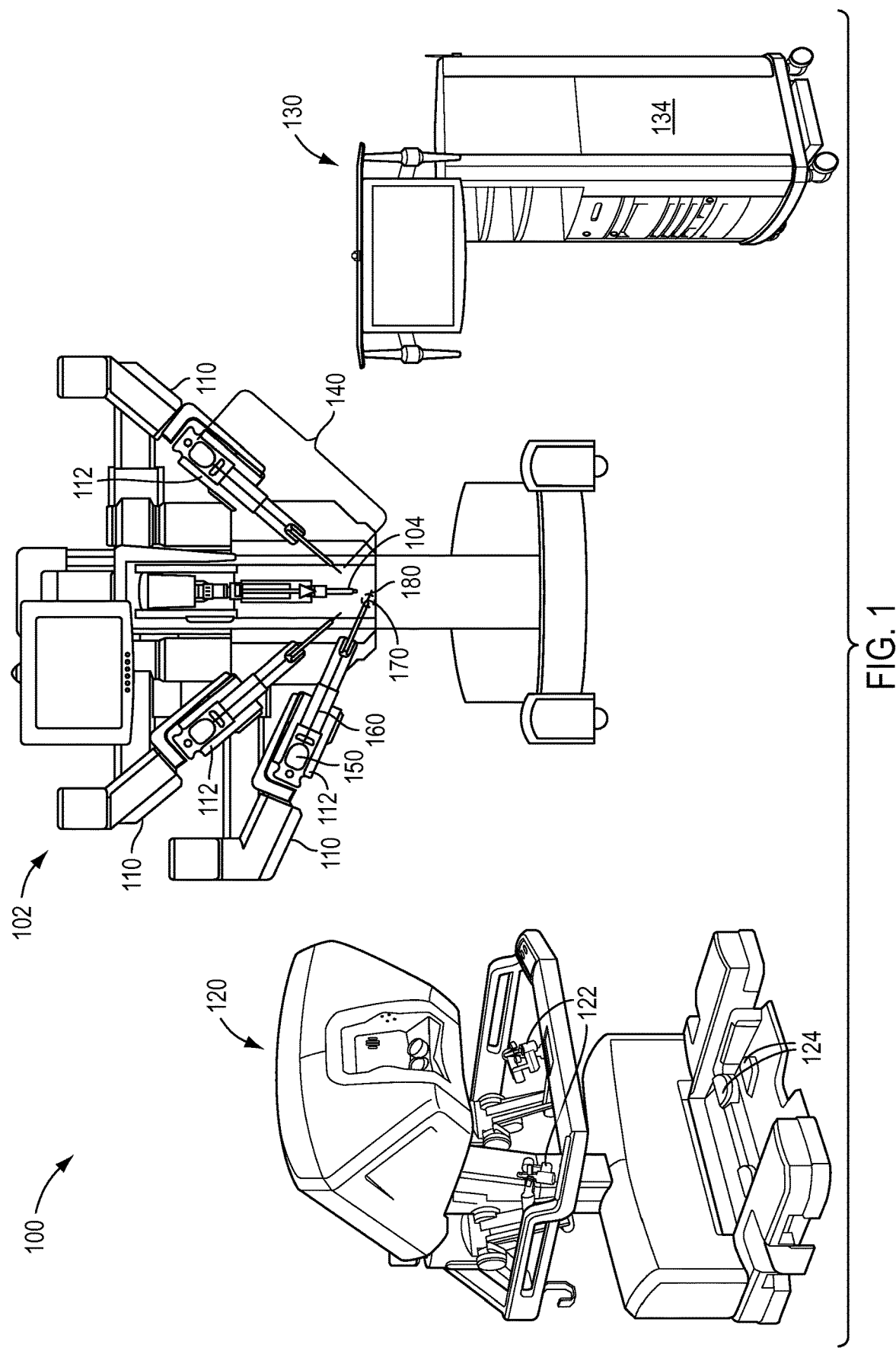
FIG. 1 is a diagrammatic view of an exemplary embodiment of a teleoperated surgical system in accordance with the present disclosure.

This description and the accompanying drawings that illustrate exemplary embodiments should not be taken as limiting. Various mechanical, compositional, structural, electrical, and operational changes may be made without departing from the scope of this description and the claims, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment. For instance, the torque distribution mechanisms and torque limitation components of various exemplary embodiments of FIG. 6 may be used with more than one of the drive mechanisms described herein.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the invention. For example, spatially relative terms— such as "beneath", "below", "lower", "above", "upper", "proximal", "distal", and the like—may be used to describe one element's or feature's relationship to another element or feature as illustrated in the figures. These spatially relative terms are intended to encompass different relative and orientations of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly.

Description of Exemplary Embodiments

In accordance with various exemplary embodiments, the present disclosure contemplates devices and methods for automatically actuating surgical instruments, such as, for example, surgical instruments for minimally invasive surgical procedures, including but not limited to teleoperated surgical instruments, during reprocessing of the surgical instruments. For instance, exemplary embodiments described herein may be used to automatically actuate and reposition a surgical instrument, or one or more components of the surgical instrument, during the reprocessing to facilitate cleaning of the instrument and the removal of material, such as, for example, biomaterial, from various surfaces of the instrument (e.g., including surfaces of the instrument that become exposed after the repositioning). The embodiments described herein may, therefore, reduce the number of manual steps required to otherwise access such surfaces of the instrument, thereby improving efficiency and saving personnel time during instrument reprocessing.

Various exemplary embodiments described herein contemplate a drive mechanism configured to couple to a transmission mechanism of the surgical instrument so as to actuate one or more distal end components of the surgical instrument during the reprocessing, and methods which utilize such devices. In various embodiments, for example, the drive mechanism is hydraulic and driven by a fluid flowing through the drive mechanism, such as, for example, a fluid used during reprocessing of the instrument.

Various exemplary methods of reprocessing a surgical instrument, or one or more components of a surgical instrument, are also contemplated in the present disclosure. For instance, various additional embodiments described herein contemplate converting a force associated with a pressurized flow of fluid, such as, for example, a cleaning solution, to a drive force sufficient to drive an input drive member of a surgical instrument transmission member; transmitting a force from the input drive member to an actuation element coupled to a distal end component of the surgical instrument; and imparting motion to the distal end component based on the force transmitted to the actuation element to expose various surfaces of the instrument to the cleaning solution. In various embodiments, for example, the cleaning solution is used to irrigate the surgical instrument during reprocessing.

Various exemplary embodiments described herein also contemplate a portable drive mechanism configured to be coupled to a transmission mechanism of the surgical instrument and carried with the surgical instrument when coupled thereto, and methods which utilize such devices. The drive mechanism can actuate one or more input disks of the transmission mechanism to actuate one or more distal end components of the surgical instrument during the reprocessing, which may occur automatically within a reprocessing unit or manually by a technician. In various embodiments, for example, the drive mechanism uses onboard stored energy, for example, a battery, pressurized fluid, or energy stored in a mechanical mechanism, for example, a wind-up clockwork motor powered by a mainspring.

Various exemplary embodiments described herein also contemplate a drive mechanism external to a reprocessing unit and configured to be coupled to a transmission mechanism of a surgical instrument within a reprocessing unit, and methods which utilize such devices. In various embodiments, for example, a seal in the reprocessing unit allows the external drive mechanism to interface with the surgical instrument within the reprocessing unit.

Various exemplary embodiments described herein further contemplate a drive mechanism capable of providing a reciprocating motion to the transmission mechanism of a surgical instrument, and methods which utilize such devices. In various embodiments, for example, the drive mechanism can actuate one or more input disks of the transmission mechanism to actuate one or more distal end components of the surgical instrument during the reprocessing. For example, the drive mechanism can actuate each input disk independently or can have features that allow for one or more input disks to be actuated in concert.

Various exemplary embodiments described herein further contemplate a drive mechanism with torque limiting features coupling to the transmission mechanism of a surgical instrument, and methods which utilize such devices. In various embodiments, the forces applied to the transmission mechanism by the drive mechanism can be regulated by the torque regulation features, for example, spring mechanisms and surfaces that slip when excessive force is received.

Various exemplary embodiments described herein also contemplate methods of coupling a drive mechanism to the transmission mechanism of a surgical instrument to allow for a full range of motion of one or more distal end components of the surgical instrument. In various embodiments, the methods allows for a full range of motion by providing, for example, rough centering of the surgical instrument to a neutral position during coupling to the drive mechanism and/or spring features in the drive mechanism to allow for actuation over a range greater than that defined by limits of the distal end component.

Various exemplary embodiments described herein further contemplate surgical instrument recognition devices and a drive mechanism that actuates a transmission mechanism of a surgical instrument, and methods which utilize such devices. In various embodiments, the recognition device can identify the surgical instrument, for example, based on user input, an identification feature of the instrument, or a configuration (e.g. size of a part of) of the instrument. For example, the drive mechanism may alter the actuation scheme and/or the torque applied (e.g. minimum and/or maximum torque applied) to the transmission mechanism based on information from the recognition device.

Various exemplary embodiments described herein also contemplate a coupling device for a drive mechanism and a transmission mechanism of a surgical instrument, and methods which utilize such devices. The drive mechanism can actuate one or more input disks of the transmission mechanism to actuate one or more distal end components of the surgical instrument during the reprocessing. In various embodiments, the drive mechanism is held in contact with the transmission mechanism for effective force transfer by the coupling device, for example, springs, magnets, and/or a pressure chamber.

Various exemplary embodiments described herein also contemplate a reprocessing unit with a brush for cleaning the surgical instrument. In various embodiments, the brush is disposed for scrubbing external surfaces of the surgical instrument, such as those located at a distal portion of the instrument. The brush can be translated and/or rotated with respect to the surgical instrument.

As is known in the art, devices used in medical procedures, such as, for example, the surgical instruments described below, may undergo reprocessing to clean, disinfect, and/or sterilize the devices, or portions of the devices, before they are used or reused, for example, in a medical procedure on a patient. Accordingly, as used herein, the term "reprocessing" refers to any process, procedure, and/or method that is used to sufficiently clean, disinfect, sterilize and/or otherwise make a surgical instrument, or a portion of a surgical instrument, patient-ready. Reprocessing devices, therefore, can include any device and/or machine that may be used for reprocessing, and in exemplary embodiments, into which a surgical instrument may be placed for reprocessing, including, but not limited to, for example, various irrigation devices and washer disinfectors available, for example, from Getinge®, Medisafe®, Steris®, Belimed®, Miele®, and Steelco®.

Although the surgical instruments described herein with relation to various exemplary embodiments may, for example, be configured for use in computer-assisted, teleoperated surgical systems (sometimes referred to as robotic surgical systems), the term "surgical instrument," as used herein, refers to various surgical instruments used in various medical procedures, including both minimally invasive procedures and general surgical procedures, and includes both teleoperated surgical instruments and manually controlled surgical instruments. Furthermore, "surgical instrument," as used herein, refers to not only therapeutic instruments that typically include end effectors or other tools (such as, for example, jaws, forceps or graspers, needle drivers, scalpels, scissors, cauterizing tools, and staplers) and are used to carry out surgical and other procedures on a patient, but also refers to, for example, endoscopic camera instruments and other sensing instruments that are utilized during the surgical procedure to provide information, (e.g., visualization, electrophysiological activity, pressure, fluid flow, and/or other sensed data) of the remote surgical site. A brief description of a teleoperated surgical system follows, and is used to illustrate an exemplary embodiment of a surgical instrument used in minimally invasive medical procedures, which may be reprocessed between procedures (i.e., prior to reuse).

With reference to FIG. 1, an example of a teleoperated surgical system 100 is shown that can employ surgical instruments in accordance with embodiments described herein. System 100, which may, for example, be a da Vinci® Surgical System available from Intuitive Surgical, Inc., includes a patient side cart 102 and multiple surgical instruments 140, each of which is mounted in a docking port on a robotic arm 110. Instruments 140 can be interchangeable, so that the instruments 140 mounted on arms 110 can be selected for a particular medical procedure or changed during a medical procedure to provide the clinical functions needed. As is well known in the art, surgical instruments 140 can include end effectors to implement many functions including, but not limited to, for example, jaws, forceps or graspers, needle drivers, scalpels, scissors, cauterizing tools, and staplers.

Figure 2:
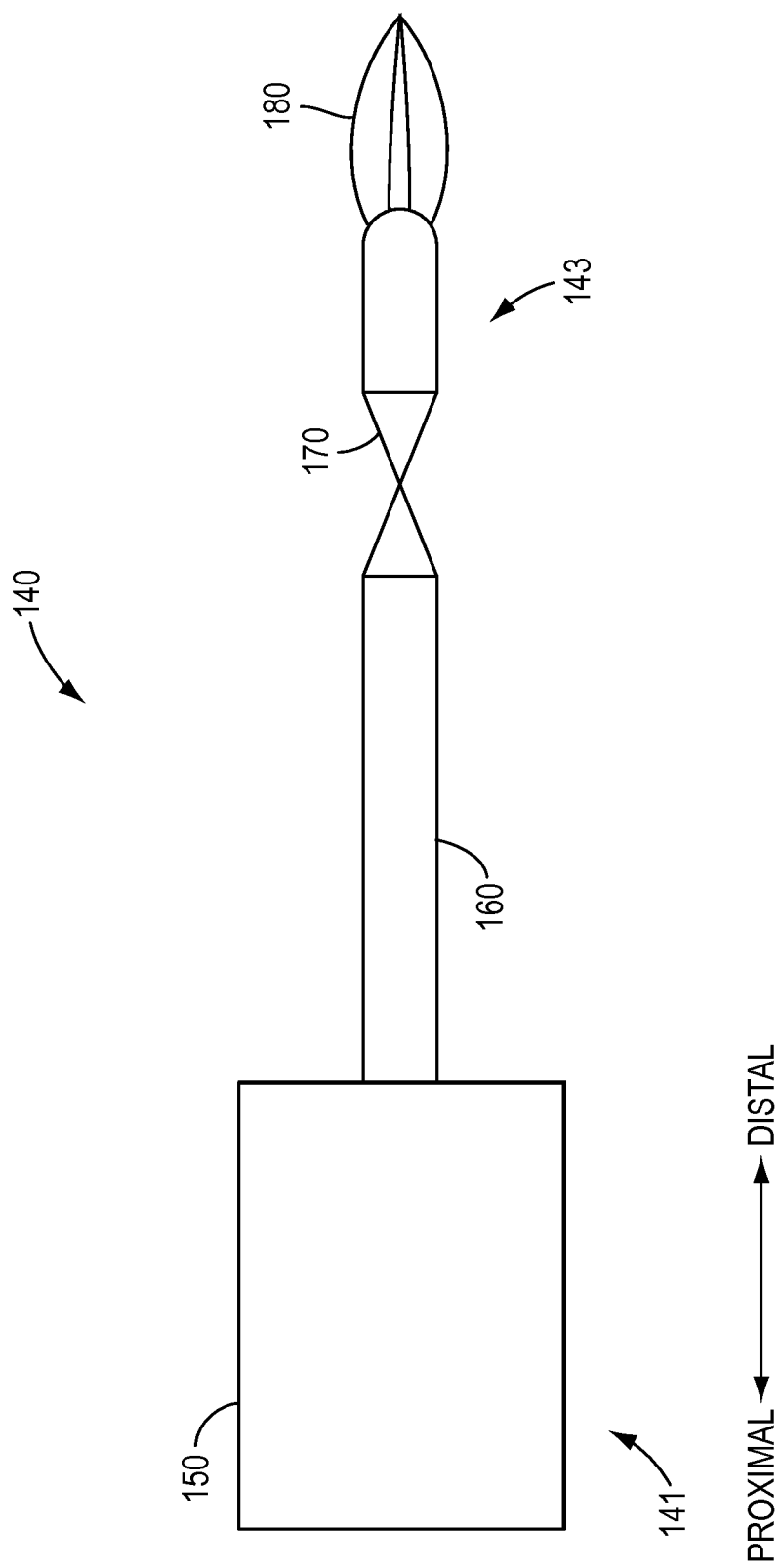
FIG. 2 is a schematic view of an exemplary embodiment of a surgical instrument in accordance with the present disclosure.

With reference to the exemplary embodiments of FIGS. 1 and 2, each instrument 140 generally includes a transmission mechanism 150 at a proximal end 141 of the instrument 140, a main shaft 160 extending from the transmission mechanism 150, an optional wrist mechanism 170 (shown best in FIGS. 2 and 3) at the distal end of main shaft 160, and an end effector 180 at a distal end 143 of the instrument 140. End effectors 180 may optionally extend from wrist mechanisms 170, if any, to provide various degrees-of-freedom (e.g., pitch and/or yaw) motion to the end effector, or end effectors 180 may extend directly from the shaft 160. Actuation elements, such as, for example, drive cables or tendons that impart motion to the end effector 180 and/or optional wrist mechanism 170 in an instrument 140 may extend through main shaft 160 and connect to transmission mechanism 150. Likewise, to the extent electrical energy or other flux is being supplied to the instruments, electrical conductors and other types of flux transmission conduits may extend through the main shaft from the proximal end of the instruments. Transmission mechanism 150 typically provides a mechanical coupling of the actuation elements to drive motors (e.g., servomotors) in the patient side robot cart 102 via input drive members (e.g., input disks) that may be coupled with output shafts of the drive motors. Cart 102 can thus control movement and forces in the actuation elements (e.g., tension tendons or cables) as needed, for example, to move or position wrist mechanism 170 and/or operate end effector 180 during a surgical procedure. Although various exemplary embodiments may utilize drive tendons or cables, those having ordinary skill in the art would appreciate that other types of actuation elements can be used to transmit forces from the transmission mechanism to the wrist and/or end effector, including, but not limited to, rods, torque tubes, etc.

The teleoperated surgical system 100 may further include a surgeon console 120 and an auxiliary control/vision cart 130. In general, the surgeon console 120 receives inputs from a user, e.g., a surgeon, by various input devices, including but not limited to, gripping mechanisms 122 and foot pedals 124, and serves as a master controller to which the instruments 140 mounted at the patient side cart 102 are responsive to implement the desired motions of the surgical instrument(s) 140, and accordingly perform the desired surgical procedure. The control/vision cart 130 includes "core" processing equipment, such as core processor 134, and/or other auxiliary processing equipment, which may be incorporated into or physically supported at the control/vision cart 130.

Figure 12:
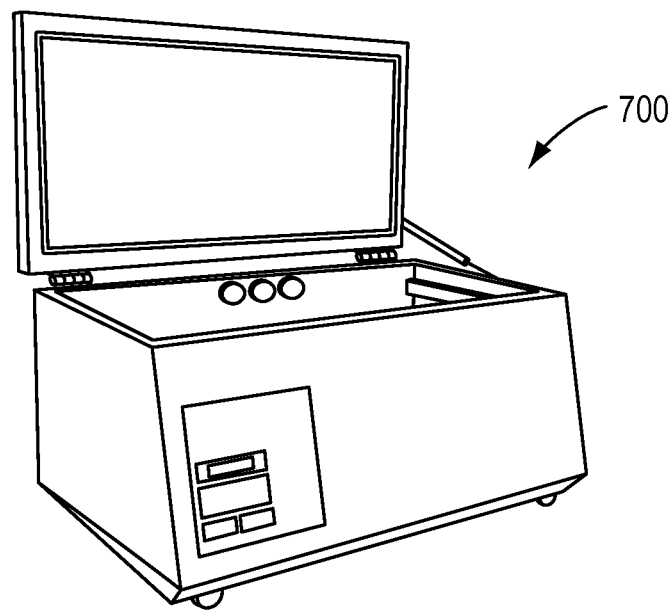
FIG. 12 is a perspective view of exemplary embodiment of a reprocessing device.

In between surgical procedures, to make surgical instruments 140 patient-ready, instruments 140 may be disconnected from the patient side cart 102 and placed, for example, within a reprocessing device, such as, for example, an automated reprocessing device 700 illustrated in FIG. 12. Various exemplary embodiments described herein contemplate portable, accessory drive devices that may be removably coupled to the transmission mechanism 150 of a surgical instrument 140 to actuate the surgical instrument 140 when the instrument is placed within the reprocessing device, and methods that utilize such devices to actuate the surgical devices 140, for example, with a force exerted by a fluid used during the reprocessing.

Drive Devices to Actuate Surgical Instruments

Figure 3:
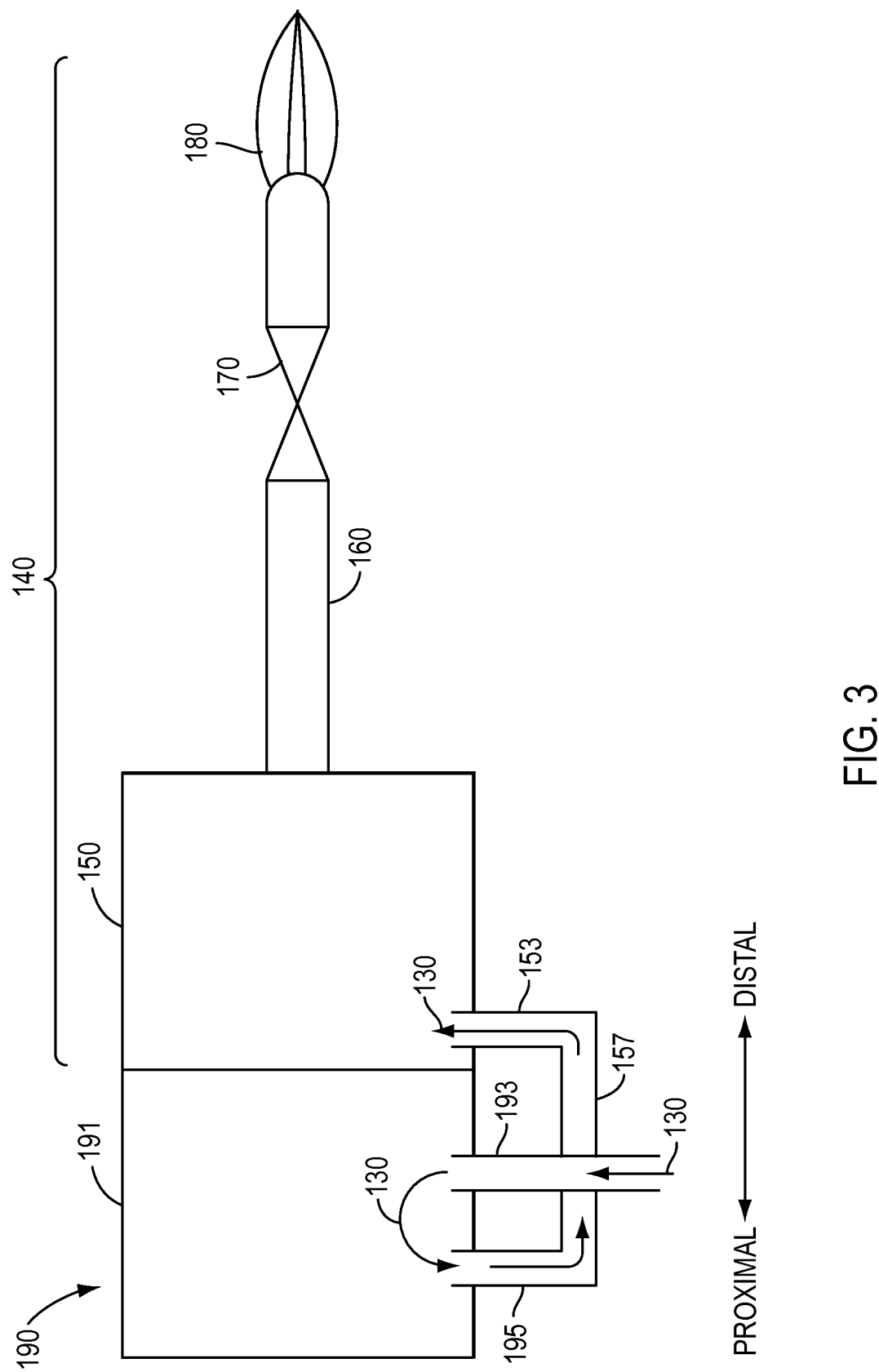
FIG. 3 is a schematic view of an exemplary embodiment of an accessory drive device for actuating a surgical instrument in accordance with the present disclosure coupled to a transmission mechanism of the surgical instrument of FIG. 2.

With reference to FIG. 3, an exemplary embodiment of an accessory drive device 190 for actuating a surgical instrument 140 is shown in a coupled state with the transmission mechanism 150 of the surgical instrument 140. The accessory drive device 190 includes a housing 191 and a drive mechanism (not shown) disposed within the housing 191. In various exemplary embodiments of the present disclosure, the drive mechanism is configured to couple to input disks 158 of the transmission mechanism 150 to drive the input disks 158 and actuate the surgical instrument 140. In various exemplary embodiments, as will be explained, the accessory drive device 190 can automatically drive the input disks 158 of the transmission mechanism 150 when the instrument 140 is placed within a reprocessing device, such as, for example, the reprocessing device 700 of FIGS. 12 and 13. According to an exemplary embodiment, accessory drive device 190 may form a part of a reprocessing unit, for example, as a portion of a sidewall of the reprocessing unit where the transmission mechanism 150 can attach, as will be discussed below.

Figure 4:
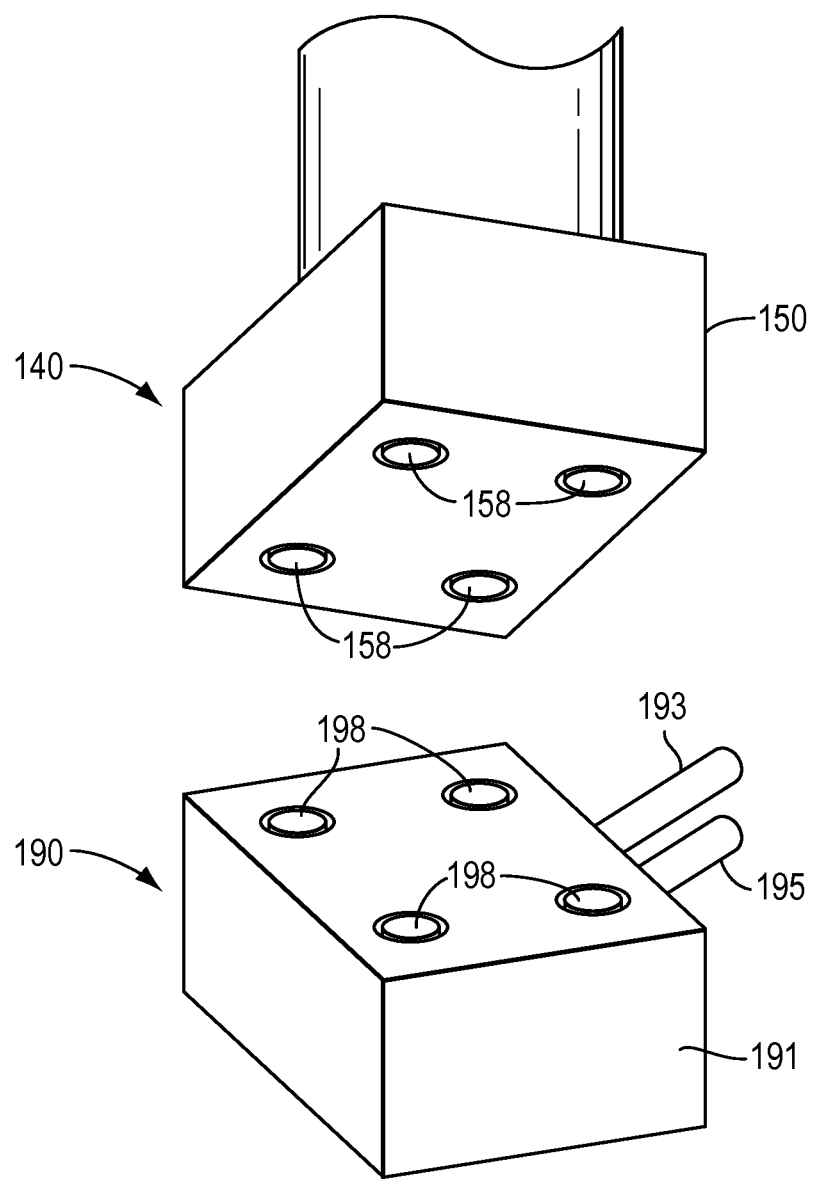
FIG. 4 is a partial schematic, perspective view showing the accessory drive device of FIG. 3 and the transmission mechanism of the surgical instrument of FIG. 2.

With reference to FIG. 4, the accessory drive device 190 includes output drive members, such as, for example, output disks 198 that are configured to couple to the input disks 158 of the transmission mechanism 150. In this manner, the transmission mechanism 150 may provide a mechanical coupling of the actuation elements of the instrument 140 to the drive mechanism of the accessory drive device 190. Thus, when coupled to the instrument 140, the accessory drive device 190 can exert forces along actuation elements (e.g., drive tendons, cables, rods, etc.) to move or position wrist mechanism 170 and/or operate end effector 180 when a motive force is provided to the drive mechanism (not shown in FIGS. 3 and 4).

Those of ordinary skill in the art would understand that the embodiment of FIG. 4 is exemplary only and that the accessory drive device 190 may have various numbers and/or configurations of output drive members, including various numbers and/or configurations of output disks 198, depending on the number and configuration of the input drive members (e.g., input disks) of the transmission mechanism to which the accessory drive device 190 couples (e.g., depending on the degrees of freedom of the surgical instrument).

In various exemplary embodiments of the present disclosure, the drive mechanism of the accessory drive device 190 is driven by a force exerted by a fluid flowing through the drive mechanism. As illustrated in FIGS. 3 and 4, in accordance with various embodiments, the accessory drive device 190 includes a fluid inlet 193 and a fluid outlet 195, and the drive mechanism is driven by a pressure exerted by a fluid 130 flowing from the fluid inlet 193, through the housing 191 and the drive mechanism, and out of the fluid outlet 195. In various exemplary embodiments, the pressure of the fluid 130 at the fluid inlet 193 may range from about 10 psi to about 60 psi, and the flow rate of the fluid 130 at the fluid inlet 193 may range from about 0.2 L/min to about 60 L/min. In another exemplary embodiment, the flow rate of the fluid 130 at the fluid inlet 193 may range from about 0.2 L/min to about 20 L/min. In various embodiments, for example, the pressure of the fluid 130 at the fluid inlet 193 is about 30 psi, and the flow rate of the fluid 130 at the fluid inlet 193 is about 30 L/min.

Although not shown, in various exemplary embodiments, fluid inlet 193 and fluid outlet 195 may be provided with various couplings that are used, for example, to provide a substantially fluid tight connection with, for example, a fluid source, including, for example, lever fittings and hose connectors, as would be understood by those of ordinary skill in the art.

The present disclosure further contemplates various methods of actuating a surgical instrument that may include one or more of the features and mechanisms of the exemplary embodiments described above to, for example, facilitate reprocessing of the instrument. An exemplary method for actuating a surgical instrument in accordance with an exemplary embodiment of the present disclosure is set forth in the following description with reference to the surgical instrument 140 and an accessory drive device 190 that includes a drive mechanism, such as, for example, one of the drive mechanisms 200, 300, 400, 500, 600 described herein with reference to FIGS. 5 and 8-11. As illustrated in FIGS. 3 and 4, the accessory drive device 190 may include, for example, a drive mechanism, and may be coupled to a transmission mechanism 150 of a surgical instrument 140. In various embodiments, for example, output disks 198 of the accessory drive device 190 may be coupled to input disks 158 of the transmission mechanism 150. The transmission mechanism 150 may, therefore, provide a mechanical coupling of the actuation elements (e.g., drive tendons, rods, torque tubes, etc.) of the instrument 140 to the drive mechanism of the accessory drive device 190.

According to various exemplary embodiments, the actuation methods described above may, therefore, further include irrigating the surgical instrument 140 with the fluid used to actuate the surgical instrument 140. Irrigating a surgical instrument may include supplying fluid to an exterior and/or interior of the surgical instrument in various manners, including but not limited to, for example, spraying, flushing, and/or soaking. An interior of the surgical instrument may be irrigated, for example, by introducing fluid used to drive the accessory drive device 190 into the surgical instrument 140 from a fluid outlet 195 of the accessory drive device 190. Fluid 130 may, for example, flow through the housing 191, the drive mechanism therein, and continue to flow into an interior of the shaft 160 of the instrument 140, from the outlet 195, to flush the interior of shaft 160. In various embodiments, for example, as illustrated in FIG. 3, the fluid outlet 195 of the accessory drive device 190 may be coupled to a flush port 153 on a distal end 141 of the instrument 140 by a flexible tube 157.

Figure 13:
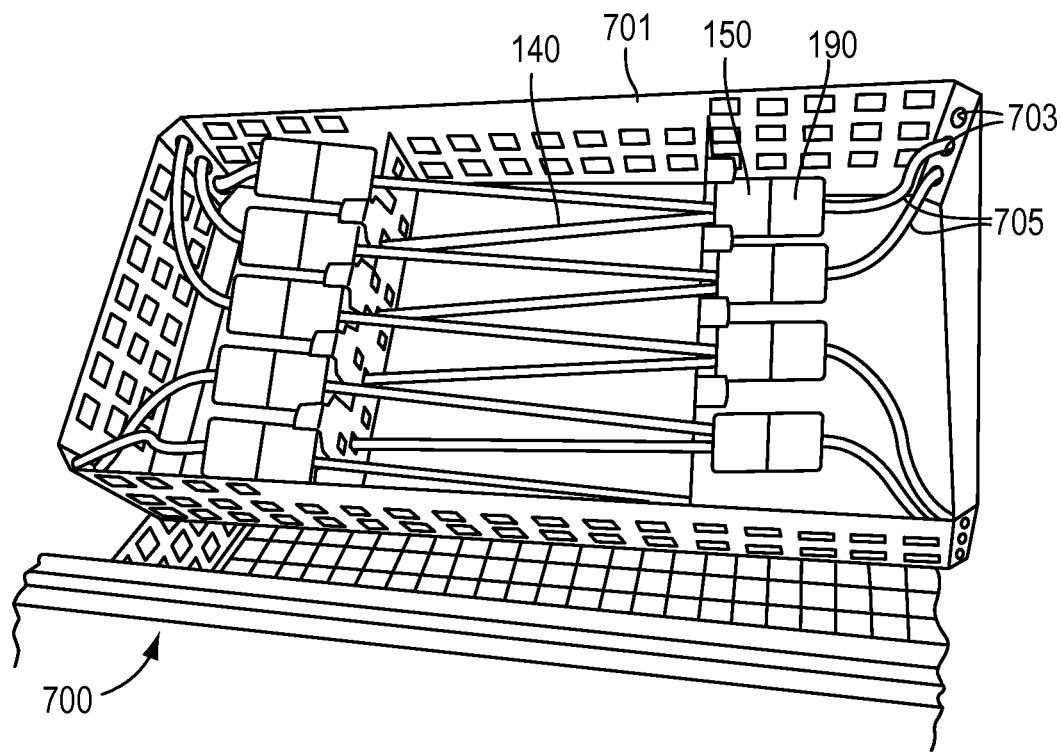
FIG. 13 is an interior perspective view of the reprocessing device of FIG. 12 shown loaded with surgical instruments and accessory drive devices, according to an exemplary embodiment.

Various exemplary methods of reprocessing a surgical instrument, which include actuating the surgical instrument during the reprocessing as described above, are also contemplated in the present disclosure. As illustrated in FIGS. 12 and 13, in various exemplary embodiments, a surgical instrument, such as, for example, the surgical instrument 140 may be positioned within a basket 701 of a reprocessing device 700. The surgical instrument 140 may then be irrigated with a cleaning fluid to clean and remove material, such as, for example, biomaterial, from the instrument 140. As above, irrigating the surgical instrument 140 may include supplying fluid to an exterior and/or interior of the surgical instrument 140 in various manners, including but not limited to, for example, spraying, flushing, and/or soaking the surgical instrument 140 within the device 700.

In various embodiments, the drive mechanism of the accessory drive device 190 is driven by a fluid within a reprocessing device, such as, for example, the device 700, during the reprocessing of the surgical instrument 140. For instance, as shown in FIG. 13, in accordance with various embodiments, the accessory drive device 190 is configured to couple to a fluid outlet 703 of the reprocessing device 700 via, for example, tubing 705 to receive a fluid from a fluid source of the reprocessing device 700 during flushing of the surgical instrument 140 in the reprocessing device 700. Thus, in various exemplary embodiments, the fluid inlet 193 of the accessory drive device 190 is configured to be coupled to the fluid outlet 703 of the reprocessing device 700, and the fluid outlet 195 of the accessory drive device 190 is configured to be in flow communication with an interior of the surgical instrument 140. In this way, the fluid may flow from the fluid source of the reprocessing device 700, through the accessory drive device 190 and drive mechanism, and into the interior of the surgical instrument 140. As illustrated in FIG. 3, for example, in various exemplary embodiments, the fluid outlet 195 of the accessory drive device 190 may be joined to a flush port 153 located at the proximal end 141 of the surgical instrument 140 by means of a flexible tube 157 fitted with the appropriate connectors (and the fluid 130 may flow into the fluid inlet 193, through the accessory drive device 190, out the fluid outlet 195, and into the flush port 153 of the instrument 140). In this manner, the accessory drive device 190 may couple to and be driven by a conventional reprocessing device, such as, for example, the device 700, without requiring modification and/or adjustment of the reprocessing device and/or reprocessing procedure, and so as to achieve automatic movement of the surgical instrument to assist in thorough cleaning during reprocessing in the reprocessing device 700.

In various embodiments, the fluid may comprise a liquid, including, for example, water (e.g., tap water), a water solution, such as a mixture of water and a detergent, and/or various other cleaning solutions used by the reprocessing device. As would be understood by those of ordinary skill in the art, however, the drive mechanism may be driven by various fluids, from various sources, and at various fluid pressures and flow rates without departing from the scope of the present disclosure and claims. In various additional embodiments, for example, the fluid may comprise a gas, such as, for example, hot air used to thermally disinfect and/or dry the surgical instrument.

In various further embodiments, the accessory drive device 190 may, for example, be hooked up to a sink or other cleaning device in which the surgical instrument is cleaned, and the drive mechanism may be driven by a fluid supplied by the sink or other fluid source used in any of a variety of cleaning procedures.

Figure 5:
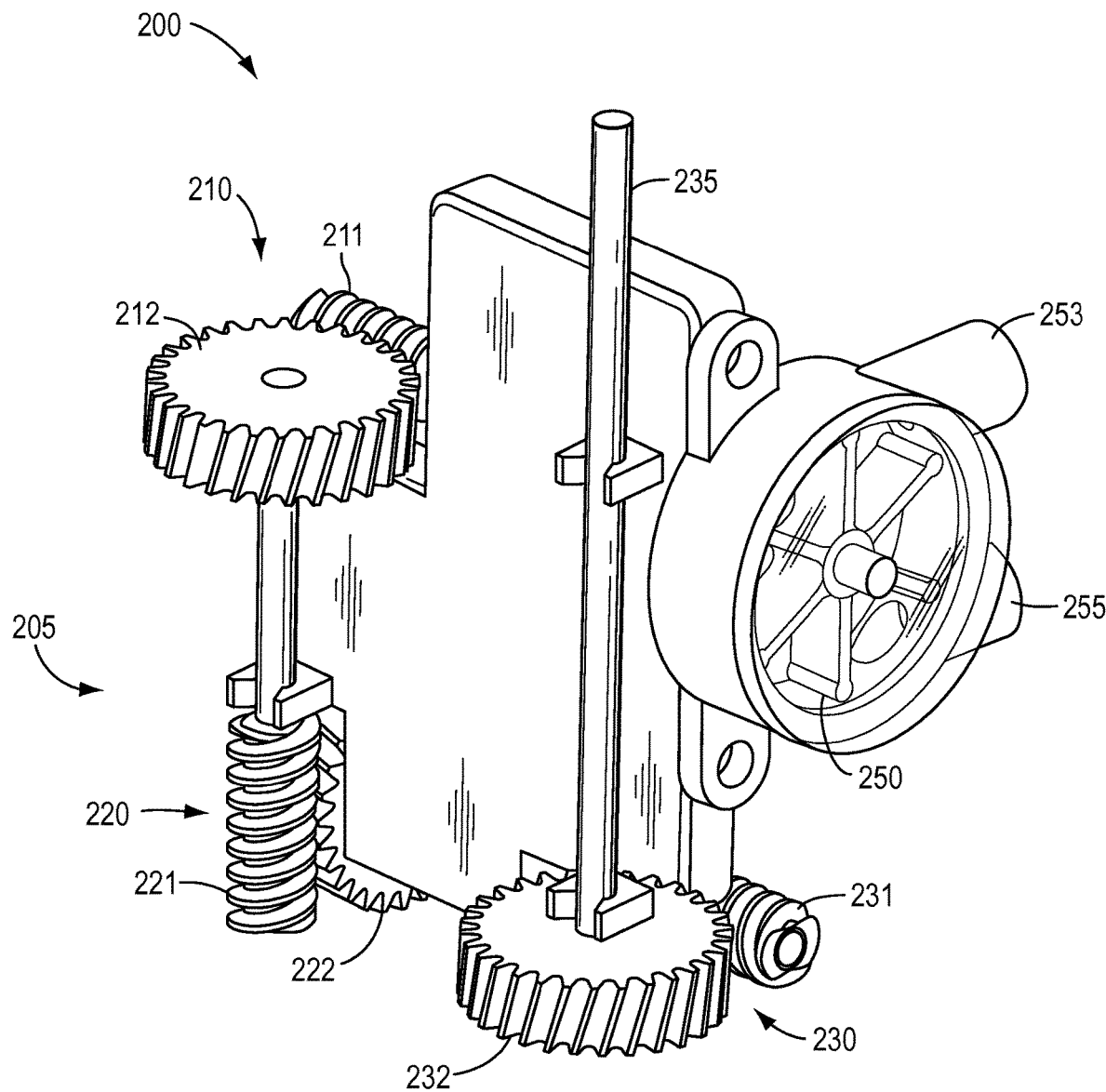
FIG. 5 is a partial, perspective view of an exemplary embodiment of a hydraulic drive mechanism in accordance with the present disclosure.

FIG. 5 illustrates one exemplary embodiment of a drive mechanism 200 in accordance with the present disclosure that can be disposed within the housing 191 for driving, for example, the output disks 198 of the accessory drive device 190. Drive mechanism 200 includes an impeller 250 and a gear box 205 including worm drives 210, 220, and 230. Each worm drive 210, 220, and 230 includes respective worms 211, 221, and 231 and worm gears 212, 222, and 232. As shown in FIG. 5, the impeller 250 is coupled to worm 211. The rotational motion of the impeller 250 is, therefore, transmitted to a drive shaft 235 of the gear box 205 via the worm drives 210, 220, and 230. In this manner, the gear box 205 may reduce the rotational speed of the impeller 250 and increase the amount of torque transmitted by the gear box 205 via the drive shaft 235. In the embodiment depicted in FIG. 5, for example, the gear box 205 may provide a speed reduction of up to about 3000:1. Various additional exemplary embodiments of the present disclosure further contemplate using a clutch mechanism (not shown) to regulate the torque of the drive shaft 235. To help prevent fatigue damage to the surgical instrument, various further exemplary embodiments of the present disclosure also contemplate using a cycle limiter mechanism (not shown) to limit the total number of motion cycles that the distal end component (e.g., wrist mechanism 170 and/or end effector 180) undergoes during reprocessing. In various exemplary embodiments, for example, the cycle limiter mechanism may limit the total number of motion cycles of the distal end component to about 1 to about 10 cycles.

As would be understood by those of ordinary skill in the art, the drive mechanism 200 may, therefore, be driven by a fluid that enters a fluid inlet 253 (which is in fluid communication with the fluid inlet 193 of the accessory drive device 190) and exits a fluid outlet 255 (which is in fluid communication with the fluid outlet 195 of the accessory drive device 190) to rotate the impeller 250, which in turn rotates the drive shaft 235 of the gear box 205.

Figure 6:
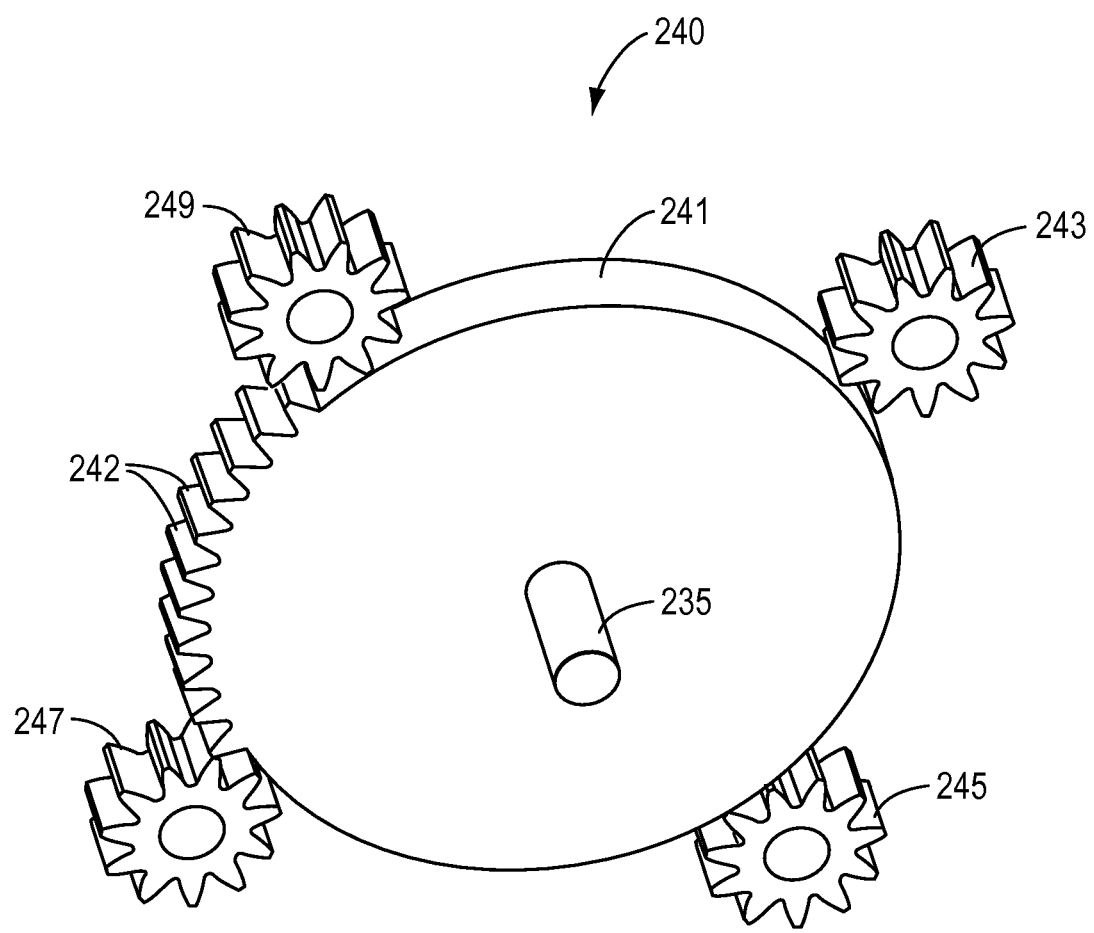
FIG. 6 is a partial, perspective view of an exemplary embodiment of a torque distribution mechanism in accordance with the present disclosure.

To transmit the torque produced by the gear box 205 to the output disks (e.g., the output disks 198), in various embodiments, the drive mechanism 200 may include a torque distribution mechanism. As illustrated in the embodiment of FIG. 6, for example, a torque distribution mechanism 240 may be coupled to the drive shaft 235 of the gear box 205. The torque distribution mechanism 240 includes a drive gear 241 and one or more pinion gears, with four pinion gears 243, 245, 247, and 249 being shown in FIG. 6. Each pinion gear 243, 245, 247, and 249 may, for example, be coupled to an output disk 198 of the accessory drive device 190, for example, through respective shafts (not shown). As shown in FIG. 6, in various exemplary embodiments, the drive gear 241 has teeth 242 over a small portion of its circumference. Thus, when the drive gear 241 rotates, each pinion gear 243, 245, 247, and 249 will rotate independently (i.e., whenever engaged by the teeth 242) to independently drive each output disk. In this manner, the drive mechanism 200 may distribute the torque produced by the gear box 205 in a sequentially timed manner among the output disks 198 as the drive gear 241 rotates, with the timing and sequence being dependent upon the spacing between the pinion gears and the configuration of the teeth 242.

Those of ordinary skill in the art would understand that the embodiment of FIG. 6 is exemplary only and that the torque distribution mechanism 240 may have various configurations, including various numbers and/or configurations of pinion gears, depending, for example, on the number of input drive members (e.g., input disks) of the transmission mechanism to which the accessory drive device 190 couples. Various embodiments of the present disclosure also contemplate grouping the pinion gears, for example, to operate multiple output disks of the accessory drive device 190 at the same time.

Figure 7A:
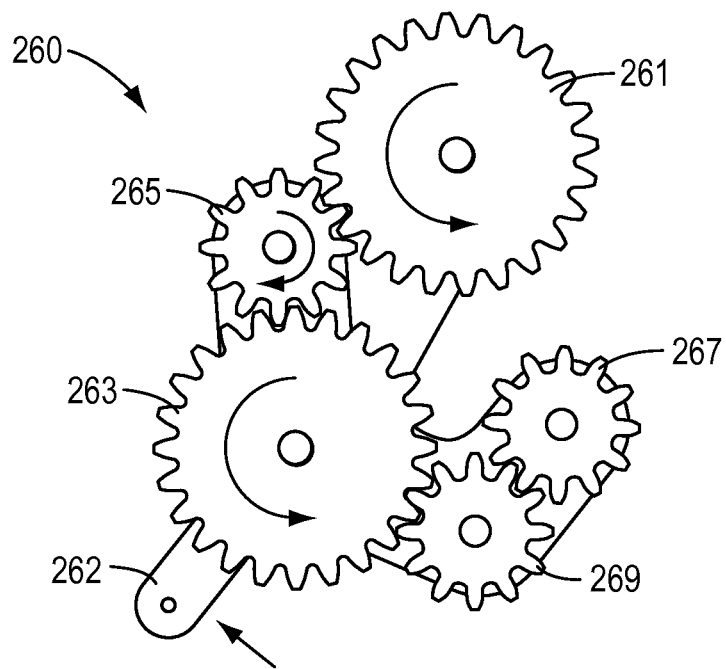
FIG. 7A is a schematic view of a reversing mechanism in accordance with the present disclosure illustrating an exemplary configuration of the reversing mechanism when the drive mechanism is producing a forward motion.
Figure 7B:
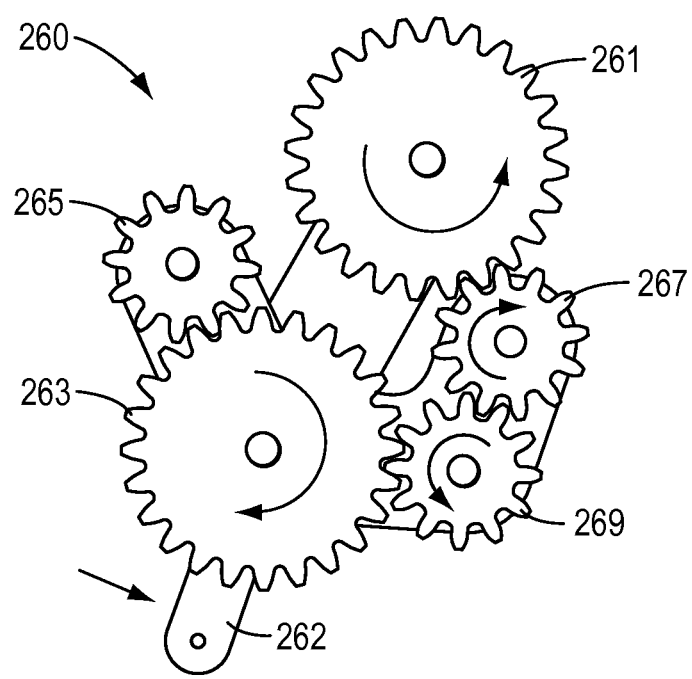
FIG. 7B is a schematic view of the reversing mechanism of FIG. 7A illustrating an exemplary configuration of the reversing mechanism when the drive mechanism is producing a reverse motion.

With reference to FIGS. 7A and 7B, in various exemplary embodiments, the drive mechanism 200 may further include a gear reversing mechanism 260 to reverse the direction of rotation of the drive gear 240 and thus the direction of motion of the output disks 198. In various exemplary embodiments, the gear reversing mechanism 260 includes drive gears 261 and 263 and pinion gears 265, 267, and 269. The pinion gears 265, 267, and 269 are carried by a carriage 262, the configuration of which can determine the direction of rotation of the drive gears 261 and 263. As illustrated in FIG. 7A, when the carriage 262 is pushed toward the left in the orientation of FIGS. 7A and 7B, the drive gears 261 and 263 are coupled by only one of the pinion gears (pinion 265), and pinion 267 is inactive. Thus, the drive gears 261 and 263 will rotate in the same direction (to produce forward motion). As illustrated in FIG. 7B, when the carriage 261 is pushed toward the right, the drive gears 261 and 263 are coupled by two of the pinion gears (pinions 267 and 269), and pinion 263 is inactive. Thus, the drive gears 261 and 263 will rotate in opposite directions (to produce reverse motion).

In various exemplary embodiments, if desired, the gear reversing mechanism 260 may be disposed in between the gear box 205 and the torque distribution mechanism 240 to reverse the direction of rotation of the drive gear 241 after, for example, one full rotation of the drive gear 241. In accordance with various embodiments, for example, the drive gear 241 may have a peg or other cam feature (not shown) protruding from the gear 241 that trips the carriage 262 (pushing the carriage toward the left or the right) after every full rotation of the gear 241.

As would be understood by those of ordinary skill in the art, the drive mechanism 200 described above and illustrated in FIGS. 5, 6, 7A, and 7B is exemplary only, and various types and configurations of drive mechanisms may be used in conjunction with the accessory drive devices of the present disclosure without departing from the scope of the present disclosure and claims.

FIGS. 8-11, 16, and 17, for example, illustrate various additional exemplary embodiments of drive mechanisms contemplated by the present disclosure to drive, for example, the output disks 198 of the accessory device 190. Those having ordinary skill in the art would appreciate, based on the disclosure herein, various other embodiments of drive mechanisms that may be used in conjunction with the accessory drive devices disclosed herein; such other drive mechanism embodiments, configurations, and modifications to the exemplary embodiments herein are considered within the scope of the present disclosure and teachings.

Figure 8:
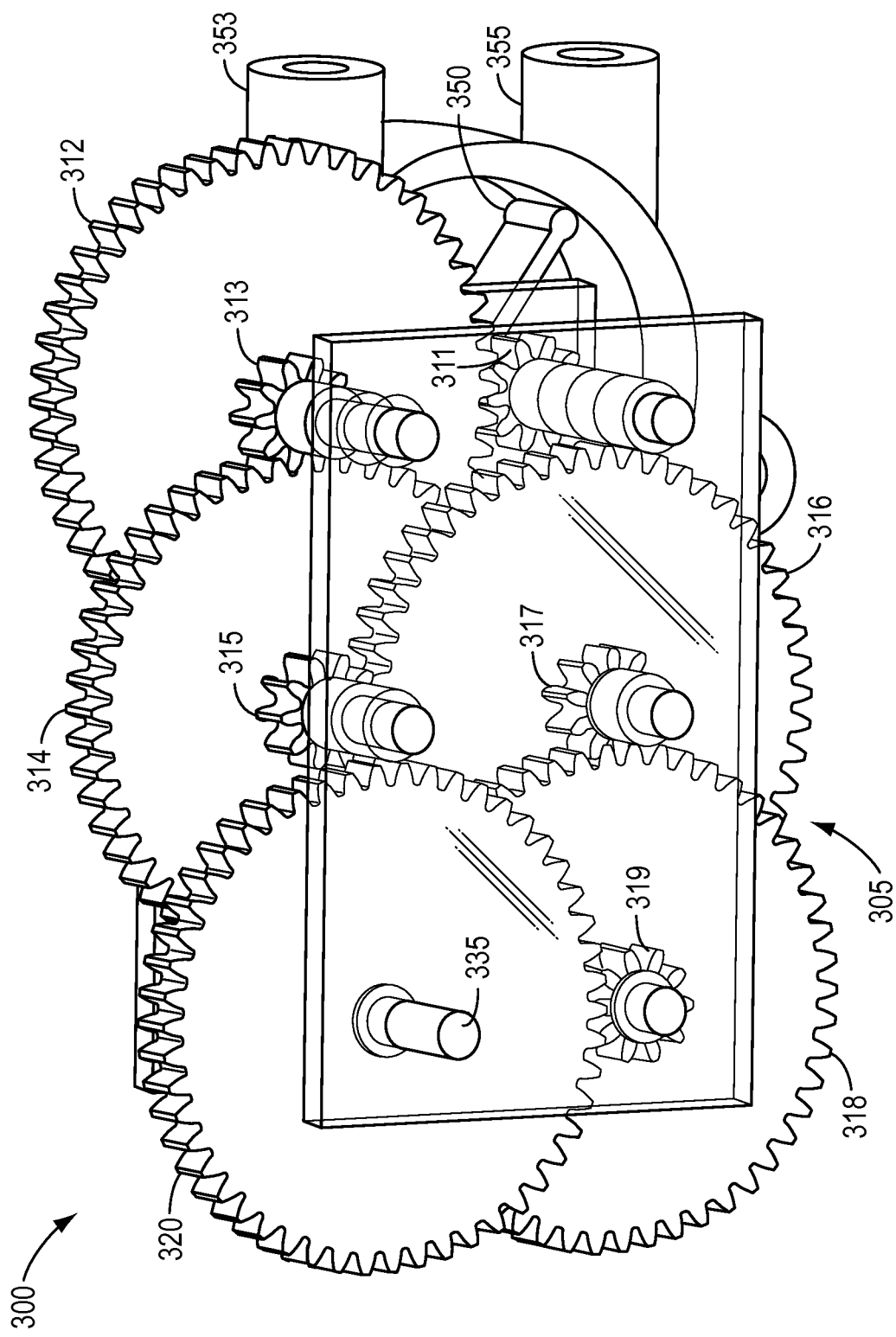
FIG. 8 is a partial, perspective view of another exemplary embodiment of a hydraulic drive mechanism of an accessory drive device in accordance with the present disclosure.

With reference to FIG. 8, a drive mechanism 300 includes an impeller 350 (shown only partially in FIG. 8) and a gear box 305 including a series of gears 311, 312, 313, 314, 315, 316, 317, 318, 319, and 320. As shown in FIG. 8, the impeller 350 is coupled to the gear 311. The rotational motion of the impeller 350 is ultimately transmitted to a drive shaft 335 of the gear box 305 via the arrangement of gears 311, 312, 313, 314, 315, 316, 317, 318, 319, and 320. Thus, in a similar manner to the gear box 205, the gear box 305 may reduce the rotational speed of the impeller 350 and increase the amount of torque transmitted by the gear box 305 to the output disks 198. The gear box 305 may be used, for example, instead of the gear box 205 when it is desirable, for example based on design constraints, to use a smaller accessory drive device (and drive mechanism). A torque distribution mechanism (not shown) as described above also may be used to distribute the torque sequentially among the output disks 198. In various exemplary embodiments, the drive mechanism 300 may also be used with a reversing mechanism (not shown) as described above with reference to FIGS. 7A and 7B, with or without a torque distribution mechanism.

Figure 16:
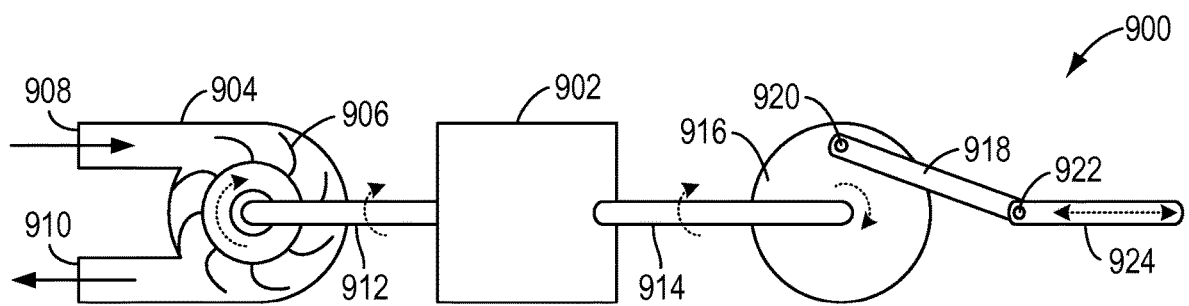
FIG. 16 is a schematic diagram of an exemplary embodiment of a hydraulic drive mechanism that provides reciprocating linear motion to the accessory drive device.

With reference to FIG. 16, an exemplary embodiment of the present disclosure further contemplates a drive mechanism 900 including a gear box 902, such as, for example, the gear box 205 or 305, driven with a hydraulic drive source 904. The drive source 904 includes an impeller 906. Fluid entering the drive mechanism via inlet 908 drives impeller 906 to provide a rotational force to gear box 902 via drive shaft 912. Spent fluid exits the hydraulic drive source 904 via outlet 910. The rotation motion of the impeller 906 is ultimately transmitted to a drive shaft 914 via one or more gears (not shown) of the gear box 902. The arrangement of gears within the gear box 902 may be such that the rotational speed from drive shaft 912 to drive shaft 914 is reduced while the amount of torque is increased. Drive shaft 914 is coupled to a flywheel 916 to cause rotation thereof. A first coupling rod 918 is attached at one end to the flywheel 916 at a rotatable connection 920 (e.g., a protrusion of the flywheel that fits into a bearing of the rod) radially displaced from a rotational axis of the flywheel and at an opposite end to a second coupling rod 924 at a rotatable connection 922 (e.g., a bolt or rivet that extends between bearings in both rods). The second coupling rod 924 can be constrained to move linearly, for example, by one or more guides (not shown), such that rotational motion of the flywheel 916 is converted to reciprocating generally linear motion of the second coupling rod 924 via the first coupling rod 918. The second coupling rod 924 can be coupled to the output disks 198 of the drive mechanism, for example, by a rack (e.g., similar to rack 1408 in FIG. 22) to drive input disks 158 of the transmission mechanism of the surgical instrument in a reciprocating fashion.

Figure 9:
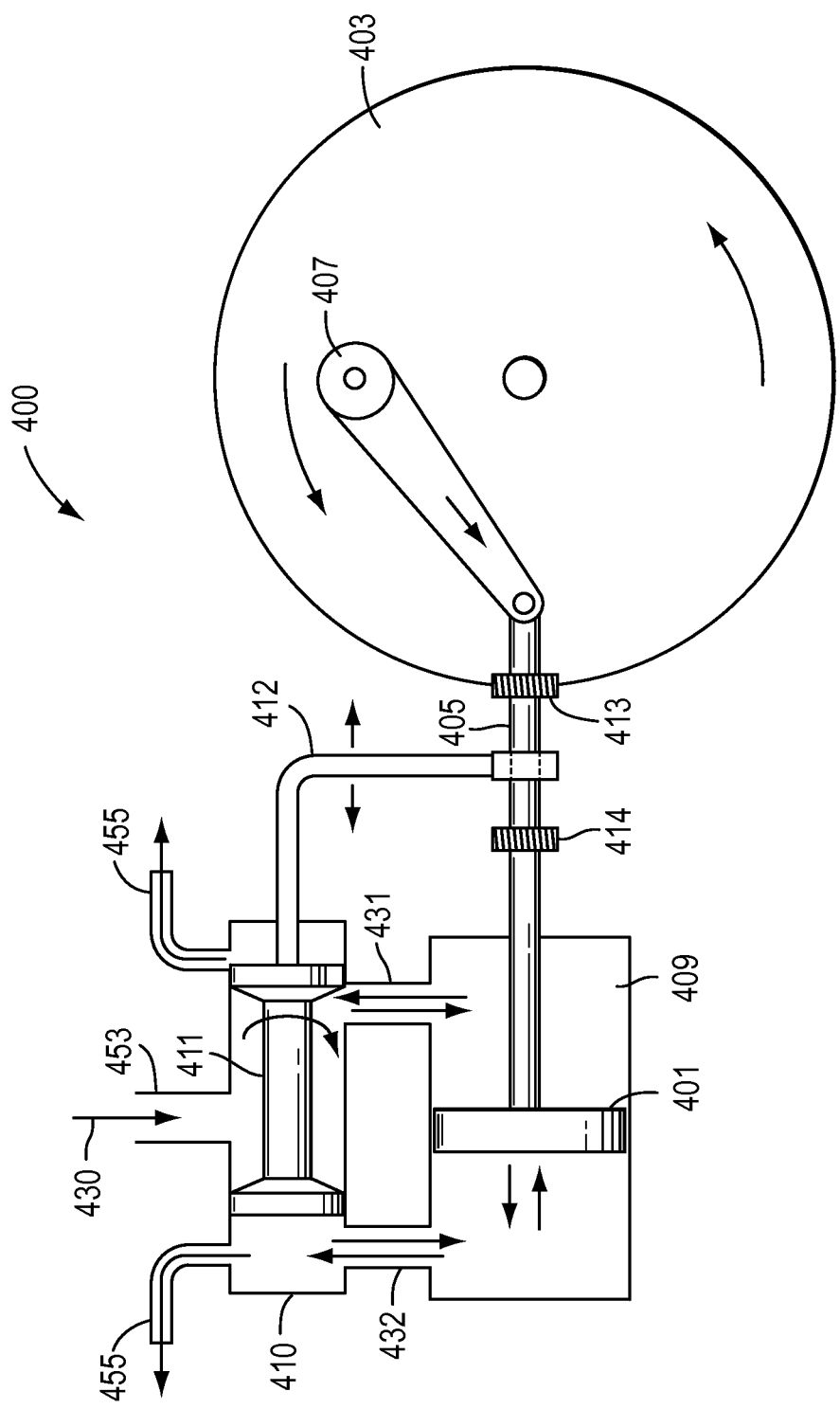
FIG. 9 is a partial, perspective view of yet another exemplary embodiment of a hydraulic drive mechanism of an accessory drive device in accordance with the present disclosure.
Figure 10:
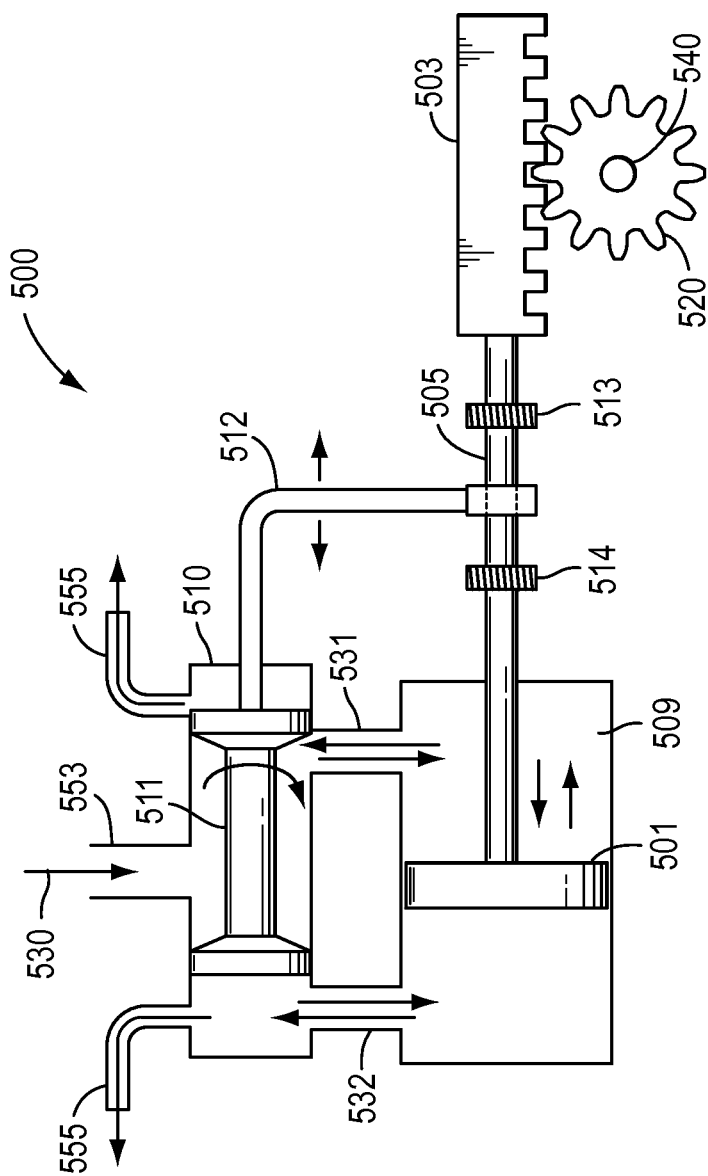
FIG. 10 is a partial, perspective view of yet another exemplary embodiment of a hydraulic drive mechanism of an accessory drive device in accordance with the present disclosure.

With reference to FIGS. 9 and 10, various exemplary embodiments of the present disclosure further contemplate driving a gear box, such as, for example, the gear box 205 or 305, with a reciprocating piston instead of an impeller 250 or 350. As illustrated in FIG. 9, for example, in various exemplary embodiments, a drive mechanism 400 may include a reciprocating piston 401 that converts fluid pressure into a rotating motion via a fly wheel 403. As those having ordinary skill in the art would have familiarity with, the piston 401 can be controlled by a valve gear 411 contained in a valve housing 410 to admit fluid into a cylinder 409 (via conduit 431 or 432) that houses the piston 401 and to allow fluid to escape the cylinder 409 (via conduit 431 or 432). The valve gear 411 is coupled, for example, via a valve arm 412 to a connecting rod 405 of the piston 401. The valve arm 412 may, therefore, be moved from side-to-side via shaft stops 413 and 414 on the connecting rod 405. That is, the connecting rod 405 moves from side-to-side to move the valve gear 411, which alternates flow between the conduits 431 and 432.

As illustrated in FIG. 9, for example, a fluid 430 may enter a fluid inlet 453 of the valve housing 410 and flow over the valve gear 411 to fill the cylinder 409 (via conduit 431 or 432). When the cylinder 409 is filled with fluid 430 via conduit 431, for example, the piston 401 is pushed to the left side of the cylinder 409. As the piston 401 nears the left side of cylinder 409, the shaft stop 413 pushes the valve arm 412 to the left, which in turn, moves the valve gear 411 to the left side of the housing 410, allowing evacuation of the fluid 430 back through conduit 431 (and ultimately out through a fluid exit 455 on the right side of the housing 410). The fluid 430 is then directed through conduit 432 to fill the left side of the cylinder 409 and push the piston 401 to the right side of the cylinder 409. As the piston 401 nears the right side of the cylinder 409, the shaft stop 414 pushes the valve arm 412 to the right, which in turn, moves the valve gear 411 to the right side of the housing 410, allowing evacuation of the fluid 430 back through conduit 432 (and ultimately out through a fluid exit 455 on the left side of the housing 410). This motion forces the flywheel 403 to turn until the valve arm 412 comes into contact with the shaft stop 414 (which completes the motion cycle). The linear (side-to-side) movement of the piston 401 is, therefore, converted to a rotating movement of the fly wheel 403 via the connecting rod 405 and a crankshaft 407 that couples the piston 401 to the fly wheel 403.

As would be understood by those of ordinary skill in the art, the drive mechanism 400 may, therefore, be driven by a fluid that enters the fluid inlet 453 (which, for example, is in fluid communication with the fluid inlet 193 of the accessory drive device 190) and exits the fluid outlets 455 (which, for example, are in fluid communication with the fluid outlet 195 of the accessory drive device 190) to operate the piston 401 and rotate the fly wheel 403.

As illustrated in FIG. 10, in various additional exemplary embodiments, a drive mechanism 500 may include a reciprocating piston 501 that converts fluid pressure into a rotating motion via a rack 503 and pinion gear 520 instead of the flywheel 403 of FIG. 9. As in the exemplary embodiment of FIG. 9, in the exemplary embodiment of FIG. 10, the piston 501 may be controlled by a valve gear 511 within a valve housing 510 to admit fluid into a cylinder 509 (via conduit 531 or 532) and allow fluid to escape the cylinder 509 (via conduit 531 or 532), thereby moving the piston 501 from side to side within the cylinder 509, and in turn pushing a valve arm 512 of the valve gear 511 back and forth between shaft stops 513 and 514 on a connecting rod 505. The linear movement of the piston 501 is converted to a rotating movement (of the pinion gear 520) via the connecting rod 505 and the rack 503 that couples the piston 501 to the pinion gear 520.

As in the exemplary embodiment of FIG. 9, in FIG. 10, the drive mechanism 500 may, therefore, be driven by a fluid 530 that enters a fluid inlet 553 (which, for example, is in fluid communication with the fluid inlet 193 of the accessory drive device 190) and exits fluid outlets 555 (which, for example, are in fluid communication with the fluid outlet 195 of the accessory drive device 190) to operate the piston 501 to move the rack 503 and rotate the pinion gear 520.

A torque distribution mechanism (not shown in FIGS. 9 and 10) as described above also may be used to distribute the torque produced by the drive mechanisms of FIGS. 9 and 10 among the output disks 198. The torque distribution mechanism may, for example, be coupled to a drive shaft (not shown) of the flywheel 403 of the embodiment of FIG. 9, or to a drive shaft 540 of the pinion gear 520 of the embodiment of FIG. 10.

Figure 11:
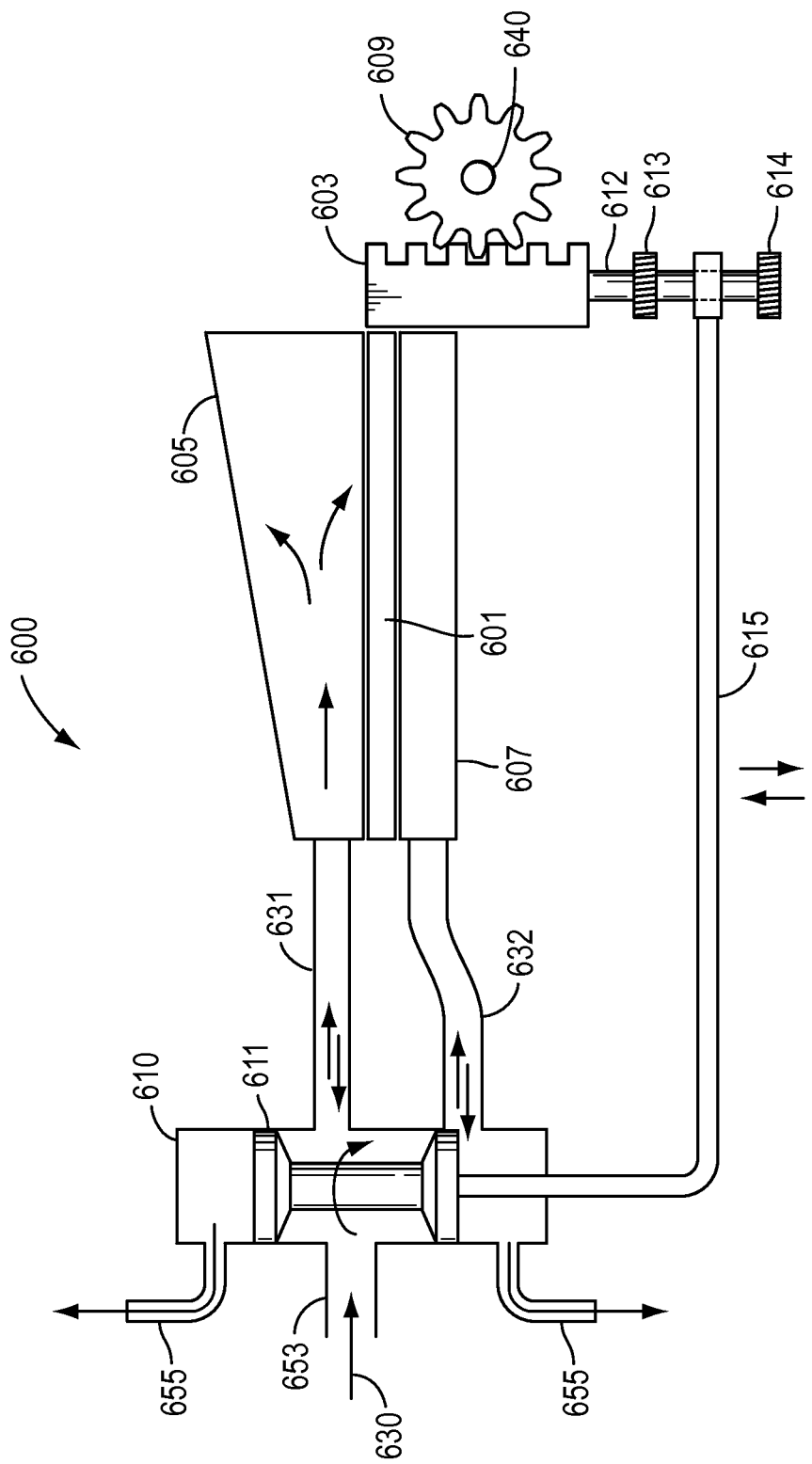
FIG. 11 is a partial, perspective view of yet another exemplary embodiment of a hydraulic drive mechanism of an accessory drive device in accordance with the present disclosure.
Figure 17:
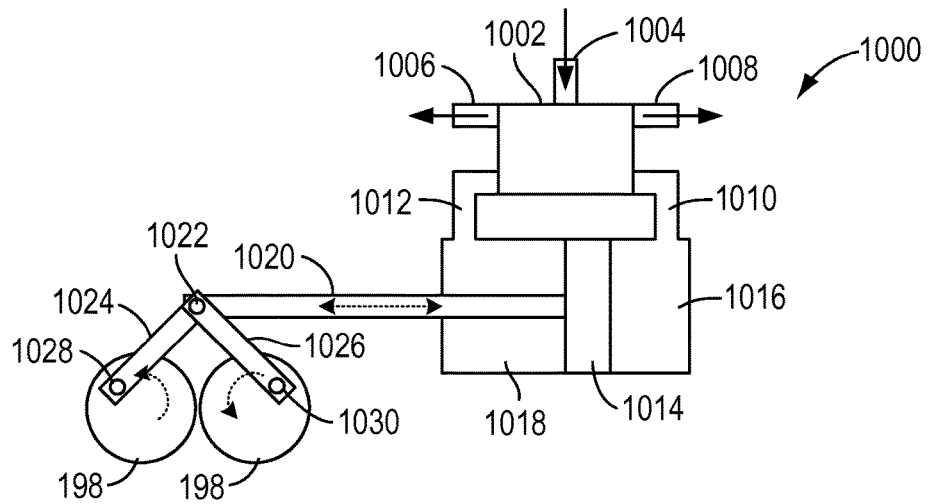
FIG. 17 is a schematic diagram of another exemplary embodiment of a hydraulic drive mechanism that provides reciprocating motion to the accessory drive device.

Various additional exemplary embodiments of the present disclosure also contemplate drive mechanisms that do not utilize gear boxes, for example, as illustrated in FIGS. 11 and 17.

With reference to FIG. 11, for example, a drive mechanism 600 includes a pair of bladders 605 and 607 and a plate 601 positioned between the bladders 605 and 607. Since the bladders 605 and 607 may have a relatively large surface area compared, for example, to an impeller or a piston, it may be possible to eliminate use of a gear box, as sufficient torque output may be attained without a gear box. In various embodiments, for example, the bladders 605 and 607 may have a surface area of, for example, about 4 square inches to about 16 square inches. In another embodiment, for example, the bladders 605 and 607 may have a surface area of about 12 square inches.

As shown in FIG. 11, the plate 601 is attached to a rack 603, which is in turn coupled to a pinion gear 609. Fluid from an inlet 653 (which, for example, is in fluid communication with the fluid inlet 193 of the accessory drive device 190) can be used to alternatively fill the bladders 605 and 607 and drive the rack 603 (via the plate 601) in a reciprocal manner, thereby rotating the pinion gear 609. In various embodiments, for example, a valve gear 611 may be used to control the flow of fluid between the bladders (i.e. to control the alternate filling and draining of each bladder 605 and 607). The valve gear 611 is coupled, for example, via a valve arm 615 to an extension shaft 612 of the rack 603. The valve arm 615 may, therefore, be moved up and down via shaft stops 613 and 614 on the extension shaft 612 (i.e., as the extension shaft 612 moves up and down) to move the valve gear 611 up and down (which alternates flow between conduits 631 and 632 and the bladders 605 and 607).

As illustrated in FIG. 11, for example, a fluid 630 may enter a fluid inlet 653 of a valve housing 610 housing the valve gear 611 and flow over the valve gear 611 to fill bladder 605 or bladder 607 (via respective conduits 631 and 632). When bladder 605 is filled with fluid 630 via conduit 631, for example, the plate 601 is pushed downward, moving the rack 603 downward. When the bladder 605 is almost completely filled (and the rack 603 nears the end of its downward travel), the shaft stop 613 pushes down on the valve arm 615, which in turn, moves the valve gear 611 to the bottom of the housing 610, allowing evacuation of the fluid 630 back through conduit 631 (and ultimately out through a fluid exit 655 at the top of the housing 610) to drain the bladder 605. The fluid 630 is then directed through conduit 632 to fill bladder 607, which pushes the plate 601 upward and moves the rack 603 upward. When the bladder 607 is almost completely filled (and the rack 603 nears the end of its upward travel), the shaft stop 614 pushes up on the valve arm 615, which in turn, moves the valve gear 611 to the top of the housing 610, allowing evacuation of the fluid 630 back through conduit 632 (and ultimately out through a fluid exit 655 at the bottom of the housing 610) to drain the bladder 607. The upward motion of the plate 601 and the rack 603, therefore, drives the pinion gear 609 until the shaft stop 614 contacts the valve arm 615 (which moves the valve gear 611 to its initial position and completes the motion cycle).

To transmit the torque produced by the bladders to the output disks (e.g., the output disks 198), in various embodiments, the drive mechanism 600 may include a torque distribution mechanism having a drive gear (not shown) that is coupled to the pinion gear 609 via a drive shaft 640. The torque distribution mechanism, for example, may be similar to the torque distribution mechanism 240 described above, and include a drive gear and four pinion gears in a planetary configuration.

As illustrated in FIG. 17, in various exemplary embodiments, a drive mechanism 1000 may include a reciprocating piston 1014 that converts fluid pressure from a fluid source 1004 into rotating motion of output disks 198 via a connecting rod 1020 and one or more slotted lever arms 1024, 1026. As those having ordinary skill in the art would have familiarity with, the piston 1014 can be controlled by a valve gear assembly 1002, for example, similar to the housing 410 with valve gears 411, 511, 611 described above with respect to FIGS. 9-11. Thus, the valve gear assembly 1002 admits fluid into one of chamber 1016 (via conduit 1010) or chamber 1018 (via conduit 1012) on opposite sides of piston 1014 and allows fluid to escape the other of the chambers 1016, 1018. The valve gear can be coupled, for example, via a valve arm to a connecting rod 1020 of the piston 1014, for example, as described with respect to FIGS. 9 and 10, or to plate 601 of FIG. 11.

The alternating fill and exhaust of chambers 1016, 1018 controlled by valve gear assembly 1002 results in a reciprocating linear motion of connecting rod 1020. Motion of an end of the connecting rod 1020 can be coupled to one or more of the output disks 198 of the drive mechanism via respective lever arms 1024, 1026. The lever arm 1024 can be coupled at one end (e.g., at pivot location 1028) to a first one of the output disks 198 and at an opposite end (e.g., at pivot location 1022) to the linearly moving connecting rod 1020. Similarly, the lever arm 1026 can be coupled at one end (e.g., at pivot location 1030) to a second one of the output disks 198 and at an opposite end (e.g., at pivot location 1022) to the linearly moving connecting rod 1020. For example, each lever arm 1024, 1026 may comprise one or more slots (not shown) that accommodate changes in distance between pivot location 1022 and pivot locations 1028, 1030 during movement of the coupling rod and the input disks so as to maintain coupling of the respective arm 1024, 1026 to the output disk 198 and the connecting rod 1020 without restricting motions thereof.

As would be understood by those of ordinary skill in the art, the drive mechanism 1000 may, therefore, be driven by a fluid that enters the fluid inlet 1004 (which, for example, is in fluid communication with the fluid inlet 193 of the accessory drive device 190) and exits the fluid outlets 1006, 1008 (which, for example, are in fluid communication with the fluid outlet 195 of the accessory drive device 190) to operate the piston 1014 and rotate the output disks 198.

As explained above, the drive mechanism of the accessory drive device 190 may be driven with a force exerted by a fluid, such as, for example, a fluid flowing through the housing 191 to provide a motive force to the drive mechanism to turn output disks 198 and input disks 158, and thereby actuate a distal end component of the surgical instrument 140. In various embodiments, for example, the drive mechanism can automatically move and tension actuation elements (e.g. drive tendons) to move or position wrist mechanism 170 and/or operate end effector 180.

As described above, in various embodiments, the accessory drive device 190 may be driven by a fluid used by a reprocessing device, such as, for example, a device 700 (see FIG. 12), during the reprocessing of the surgical instrument 140. For instance, the drive mechanism may be driven by a fluid used to flush, for example, an interior of the surgical instrument 140 during the reprocessing, and may comprise a liquid, including, for example, water (e.g., tap water), a water solution, such as a mixture of water and a detergent, and/or various other cleaning solutions used by the reprocessing device 700. As would be understood by those of ordinary skill in the art, however, the accessory drive devices of the present disclosure may be driven by various fluids, from various sources, and at various fluid pressures and flow rates without departing from the scope of the present disclosure and claims.

As described above, in various exemplary embodiments, the drive mechanism of the accessory drive device 190 may be driven (i.e., to convert the fluid force) by a cleaning fluid used to irrigate the device 140. Accordingly, as illustrated in FIG. 13, in various exemplary embodiments, the cleaning fluid may be directly supplied to the accessory drive device 190 via a tube 705 connecting the device 190 to the basket 701 of the reprocessing device 700. Those of ordinary skill in the art would understand, however, that the embodiments of FIGS. 12 and 13 are exemplary only and that various types, sizes, and/or configurations of reprocessing devices may be used to irrigate a surgical instrument, and that the cleaning fluid used to irrigate the surgical instrument may be supplied (e.g., to the drive mechanism) in various ways, without departing from the scope of the present disclosure. In various embodiments, for example, the accessory drive device may be directly connected to the reprocessing device 700.

Portable Drive Devices

Figure 15:
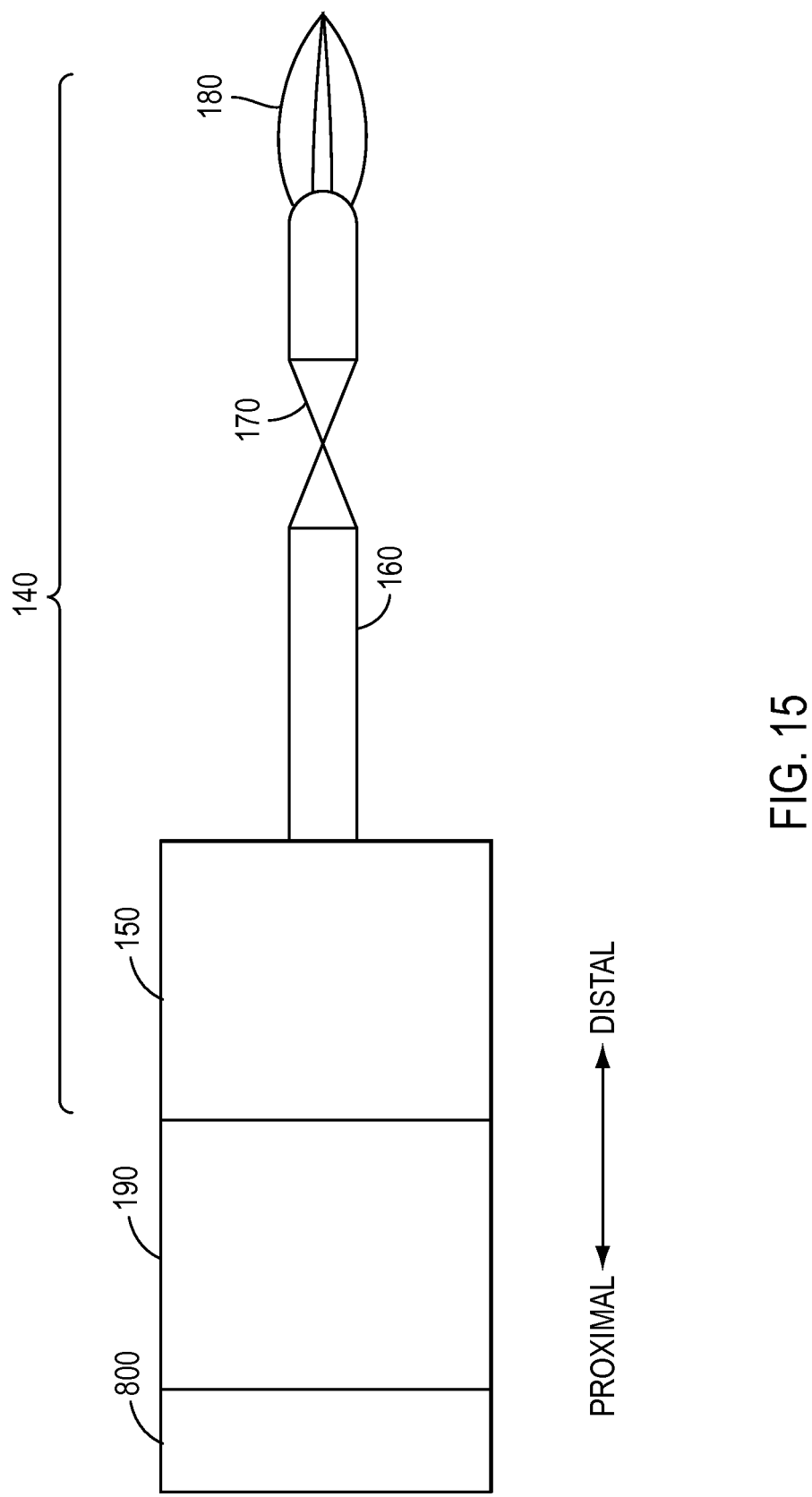
FIG. 15 is a schematic view of an exemplary embodiment of a motor pack for driving an accessory drive device in accordance with the present disclosure coupled to the accessory drive device of FIG. 3.

Those of ordinary skill in the art would further understand that while the exemplary drive mechanisms described above are driven by a fluid, such as, for example, a fluid used during the reprocessing of the surgical instrument, the drive mechanisms described herein may be driven using various methods and/or techniques, while utilizing various energy sources. For example, as illustrated in FIG. 15, various exemplary embodiments of the present disclosure contemplate using a detachable motor pack 800, such as, for example, a motor pack containing an onboard stored energy source, to power the drive mechanism and actuate the surgical instrument during, for example, the irrigation, rather than using the motive force provided by fluid flow. For example, the motor pack can be powered by batteries (e.g., replaceable or rechargeable), a pressurized fluid source (e.g., $CO_2$ cartridges), or a mechanical energy storage mechanism (e.g., a wind-up clockwork motor powered by a mainspring).

The motor pack 800 can thus be attached to accessory drive device 190 and transmission mechanism 150 such that the entire assembly can be carried (e.g., portable) with the surgical instrument 140. For example, the motor pack 800 may be attached to the surgical instrument 140 external to a reprocessing unit and then the assembly installed in the reprocessing unit for subsequent reprocessing. Alternatively, the motor pack 800 may be a replaceable unit inserted in an interior of the reprocessing unit and upon which the surgical instrument 140 is installed for subsequent reprocessing. After reprocessing of the surgical instrument 140, or after the energy storage has been depleted, the motor pack 800 can be removed from the reprocessing unit for replenishment (e.g., recharging or replacement of batteries, rewinding, etc.).

Figure 18:
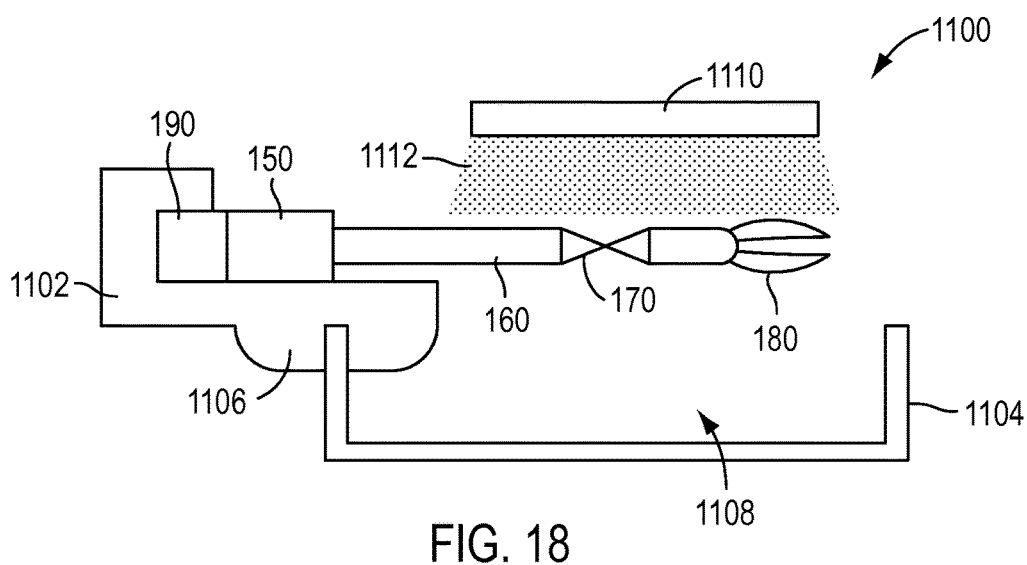
FIG. 18 is a schematic diagram of an exemplary embodiment of a manual reprocessing mount with motor pack for driving an accessory drive device.

In another alternative, the motor pack 800 can be used by a technician to automatically actuate the end effector of the 180 of the instrument 140 during manual reprocessing. For example, with reference to FIG. 18, an exemplary embodiment 1100 of a drive mechanism 1102 for an accessory device 190 for actuating a surgical instrument is shown in a coupled state with a transmission mechanism 150 of the surgical instrument. The drive mechanism 1102 is configured as a supporting arm with a mounting portion 1106 that can attach to, for example, an edge of a sink 1104 or other reprocessing receptacle. The drive mechanism 1102 supports the surgical instrument, for example, shaft 160, wrist 170, and end effector 180, over a basin 1108 of the sink 1104 so as to receive runoff from the surgical instrument during irrigation by fluid 1112 from a fluid source 1110. A technician can thus position the fluid source 1110 to irrigate different portions of the surgical instrument or different surgical instruments, or to use additional cleaning tools (e.g., a brush to scrub exterior surfaces of the surgical instrument), without having to manually support the surgical instrument over the basin 1108. As in the other embodiments described above, the drive mechanism 1102 can drive the accessory drive device 190, for example, to automatically actuate the end effector of the surgical instrument so that the technician has free hands to control cleaning tools to effect reprocessing. Alternatively or additionally, the drive mechanism 1102 can include a fluid connection that interfaces with an appropriate inlet on the surgical instrument for irrigating internal surfaces thereof.

Drive Mechanism Seals

Figure 19A:
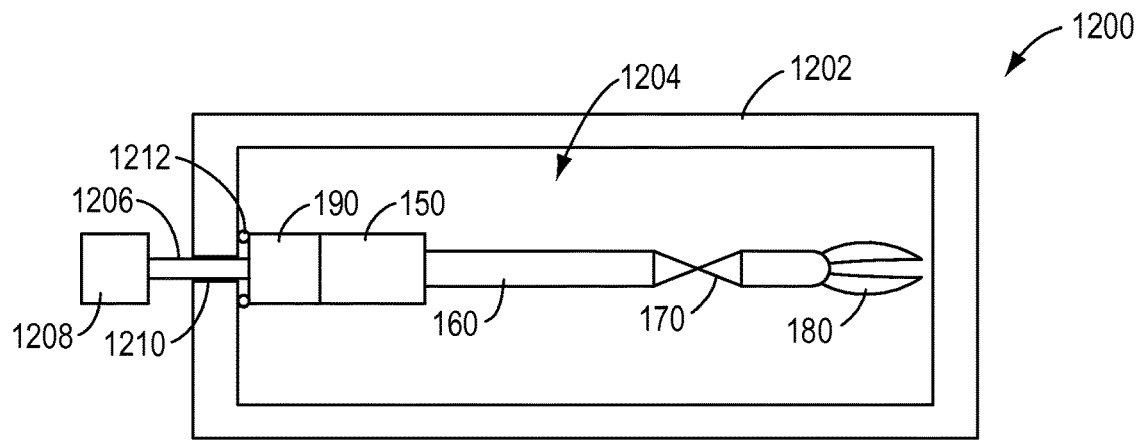
FIG. 19A is a schematic diagram of an exemplary embodiment of a reprocessing system with a drive mechanism component situated external to an interior of the reprocessing device.

Those of ordinary skill in the art would further understand that while the exemplary drive mechanisms described above are disposed in the same environment as the surgical instrument being reprocessed, such as, for example, within a reprocessing unit and therefore subject to reprocessing fluid, the drive mechanisms described herein may alternatively be situated in a different environment than the surgical instrument. For example, as illustrated in FIG. 19A, an exemplary embodiment of the present disclosure contemplates a reprocessing setup 1200 with a drive source 1208 arranged outside a reprocessing unit 1202 and thus isolated from the environment 1204 to which the surgical instrument is exposed. For example, components within the environment 1204 internal to the reprocessing unit 1202 could be subjected to fluids, such as cleaning fluids, having a pH less than 11, for example, between 7 and 11, as well as elevated temperatures, for example, up to 55° C. during reprocessing, or up to 93° C. during a final rinse cycle.

Various components of the surgical instrument can be disposed within the environment 1204 to effect reprocessing of the instrument, for example, transmission mechanism 150, shaft 160, wrist mechanism 170, and end effector 180. An accessory drive 190 for interfacing with the transmission mechanism 150 may also be disposed within environment 1204. Alternatively, accessory drive device 190 may form a part of the reprocessing unit 1202, for example, as a portion of a sidewall of the unit 1202 where the transmission mechanism 150 of the surgical instrument can attach.

A drive source 1208 can provide power to the accessory drive 190, for example, as rotation of one or more drive shafts 1206 which extends through a conduit 1210 in a sidewall of the reprocessing unit 1202, and in turn actuate the end effector via actuation of the transmission mechanism. One or more seals 1212 can be provided at internal or external edges of the conduit 1210 in order to prevent fluids and/or other contents of the environment (e.g., biological material removed from the surgical instrument during reprocessing) from exiting the reprocessing unit 1202 or contacting the drive source 1208. For example, the drive source 1208 can be a hydraulic drive (for example, one of the hydraulic drives described above) or an electric motor drive (for example, one or more DC motors configured to rotate, independently or in groups, the individual input disks 158 of the transmission mechanism 150).

Figure 19B:
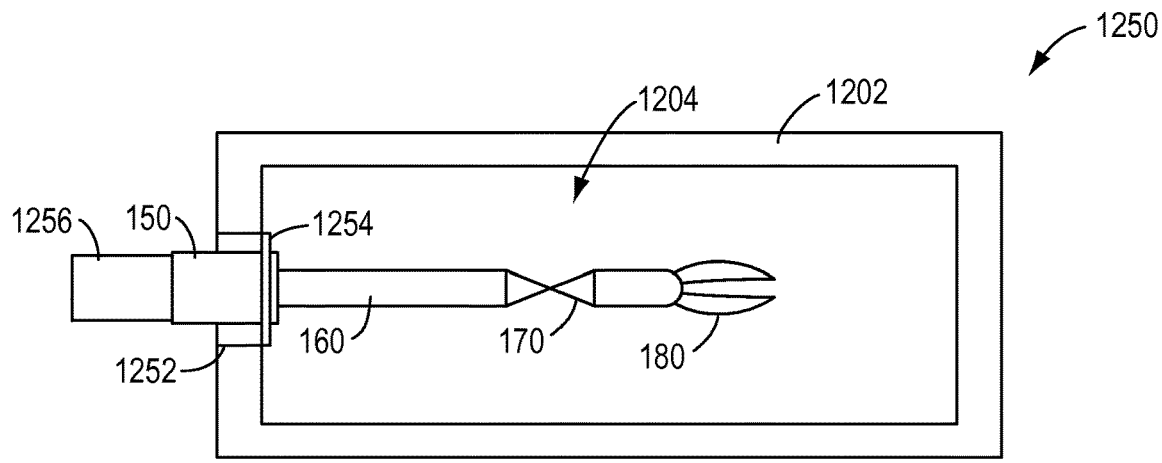
FIG. 19B is a schematic diagram of an exemplary embodiment of a reprocessing system with the accessory drive device of the surgical instrument situated external to an interior of the reprocessing device.

As illustrated in FIG. 19B, an exemplary embodiment of the present disclosure further contemplates a reprocessing setup 1250 with both drive mechanism 1256 and a transmission mechanism 150 of the surgical instrument arranged outside a reprocessing unit 1202 and thus isolated from the environment 1204 to which the surgical instrument is exposed. In contrast to the embodiment of FIG. 19A, only the shaft 160, wrist mechanism 170, and end effector 180 of the surgical instrument are maintained within the reprocessing environment 1204. The drive mechanism 1256 interfaces with the transmission mechanism 150, both of which are sealed from the internal environment 1204 by one or more seals 1254 provided at internal or external edges of conduit 1252 in a wall of the reprocessing unit 1202. The one or more seals 1254 can prevent fluids and/or other contents of the environment (e.g., biological material removed from the surgical instrument during reprocessing) from exiting the reprocessing unit 1202 or contacting the drive mechanism 1256 and/or the transmission mechanism 150.

The drive mechanism 1256 can include a drive source that rotates various drive disks contacted with input disks of the transmission mechanism to thereby actuate the end effector 180 of the surgical instrument. For example, the drive mechanism 1256 can be a hydraulic drive in combination with an accessory drive (for example, one of the hydraulic drives described above) or an electric motor drive (for example, one or more DC motors configured to independently rotate the individual input disks 158 of the transmission mechanism 150). Alternatively, since both the drive and transmission mechanisms remain isolated from the harsh internal environment 1204 of the reprocessing unit 1202, the drive mechanism 1256 can comprise the same drive system employed for controlling the surgical instrument during a surgical operation, for example, as may be used for a manually operated instrument or a motor pack used to drive various degrees-of-freedom of a teleoperated instrument. The drive system may be configured, for example, via programming stored in a memory thereof, to move the end effector in a specified manner during reprocessing.

Actuation of Surgical Instrument During Reprocessing

In accordance with the present disclosure, the surgical instrument 140 may be actuated during the irrigation, for example, to expose various and differing surfaces of the instrument 140 to the cleaning fluid. To actuate the surgical instrument 140, in various exemplary embodiments, a force associated with a flow of fluid may be converted to a drive force sufficient to drive an input drive member of a surgical instrument transmission mechanism, such as, for example, an input disk 158 of the transmission mechanism 150 of the exemplary embodiment of FIGS. 2-4. A force from the input disk 158 may be transmitted to an actuation element (e.g., drive tendon, rod, torque tube, etc.) coupled to a distal end component, such as, for example, a wrist mechanism 170 and/or an end effector 180, of the surgical instrument 140. Motion may then be imparted to the distal end component based on the force transmitted to the actuation element. As described above, in various exemplary embodiments, an accessory drive device 190, including a drive mechanism 200, 300, 400, 500, 600, may be used to convert the fluid force to automatically exert forces on the actuation elements of the instrument 140 to impart motion to the wrist mechanism 170 and/or the end effector 180 of the instrument 140 during the irrigation. In various embodiments, the accessory drive device 190 may repeatedly actuate and/or impart motion to the wrist mechanism 170 and/or the end effector 180 throughout the duration of the irrigation cycle of the reprocessing device 700, for example, cycling the wrist mechanism 170 and/or end effector 180 through their full ranges of motion (through both forward and reverse motion cycles) at least about 4 times during an irrigation cycle of about 10 to 30 minutes.

Figure 14A:
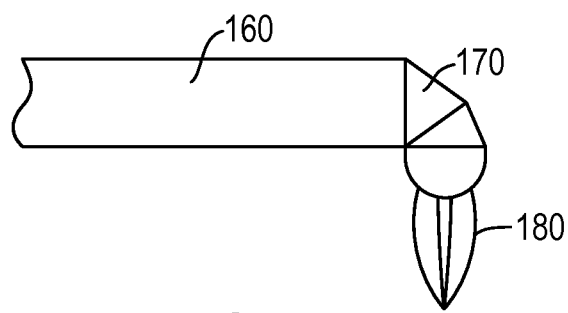
FIGS. 14A-14D are partial, schematic views showing the surgical instrument of FIG. 2 going through a motion cycle.
Figure 14B:
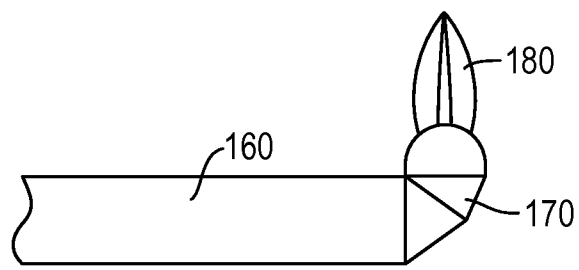
Figure 14C:
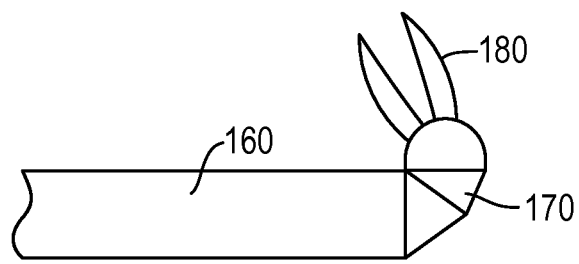
Figure 14D:
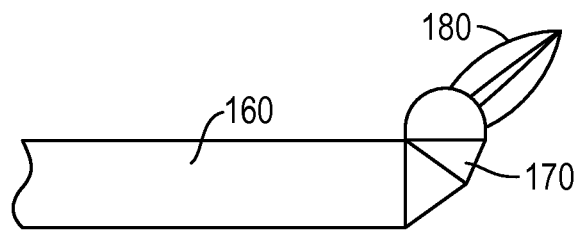

One exemplary embodiment of the present disclosure for distributing torque and actuating a surgical instrument 140 comprising a wrist mechanism 170 and a jawed end effector 180 (e.g., jaws as illustrated in FIGS. 2 and 3) utilizing the torque distribution mechanism of FIG. 6 will now be described with reference to FIGS. 14A-14D (which shows the surgical instrument 140 going through a motion cycle). When the teeth 242 of the drive gear 241 engage and impart motion to the pinion gear 249, as illustrated in FIG. 14A, the wrist 170 may undergo a pitch movement of about 180 degrees in one direction. When the teeth 242 of the drive gear 241 engage and impart motion to the pinion gear 243, the shaft 160 may undergo a roll movement of about 180 degrees in one direction as illustrated in FIG. 14B. When the teeth 242 of the drive gear 241 engage and impart motion to the pinion gear 245, the wrist 170 may undergo a yaw movement, opening the jaws and moving the jaws to one side as illustrated in FIG. 14C. Finally, when the teeth 242 of the drive gear 241 engage and impart motion to the pinion gear 247, as illustrated in FIG. 14D, the wrist 170 may undergo a yaw movement, closing the jaws and moving the jaws to the opposite side. After completion of this motion cycle, the cycle may then be reversed, for example, by employing the reversing mechanism illustrated in FIGS. 7A and 7B. In this manner, the distal end components of the surgical instrument 140 (e.g., wrist mechanism 170 and/or end effector 180) may go through their full ranges of motion, thereby exposing various and differing surfaces of each component to the cleaning fluid during the reprocessing.

Those of ordinary skill in the art would understand that FIGS. 14A-14D are intended to illustrate one exemplary motion cycle for the surgical instrument 140, and that a variety of other motion cycles, using various types and/or configurations of torque distribution devices, may be employed depending, for example, on the type and/or configuration of surgical instrument to be actuated, without departing from the scope of the present disclosure.

Reciprocating Drives

Figure 20:
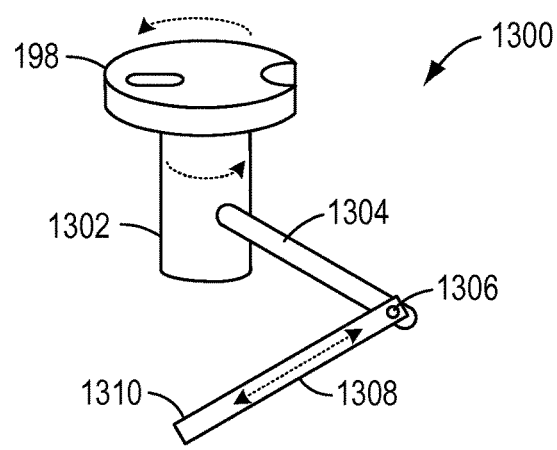
FIG. 20 is a perspective view of an exemplary embodiment of a coupling to a drive disk of the drive mechanism that coverts motion of a drive source into rotational motion of the drive disk via an arm.

Those of ordinary skill in the art would further understand that reciprocating actuation of the input disks of the transmission mechanism of the surgical instrument can be provided using various methods and/or techniques. Reciprocating motion during reprocessing may be desirable to limit the range of motion the instrument undergoes and also to promote thorough cleaning of various surfaces. For example, as illustrated in FIG. 20, various embodiments of the present disclosure contemplate a coupling 1300 that uses an arm 1304 directly connected to a shaft 1302 of the output disk 198 to impart a reciprocating rotation thereto. The arm 1304 extends from the shaft 1302 and is connected to a connecting rod 1308 at a pivot point 1306. A drive mechanism (not shown, e.g., drive mechanisms of any of FIGS. 9-11, 16, and 17) may impart a reciprocating linear motion (or have components of motion directed tangential with respect to the drive disk) at end 1310 of the connecting rod 1308, which thereby causes reciprocating rotation of the output disk 198. When the accessory drive includes multiple output disks 198, each output disk 198 may have its own arm 1304 so that it can be actuated independently of the other output disks 198. Alternatively, one or more of the output disks 198 may have arms 1304 coupled together so that actuation of the output disks 198 is in concert.

Figure 24:
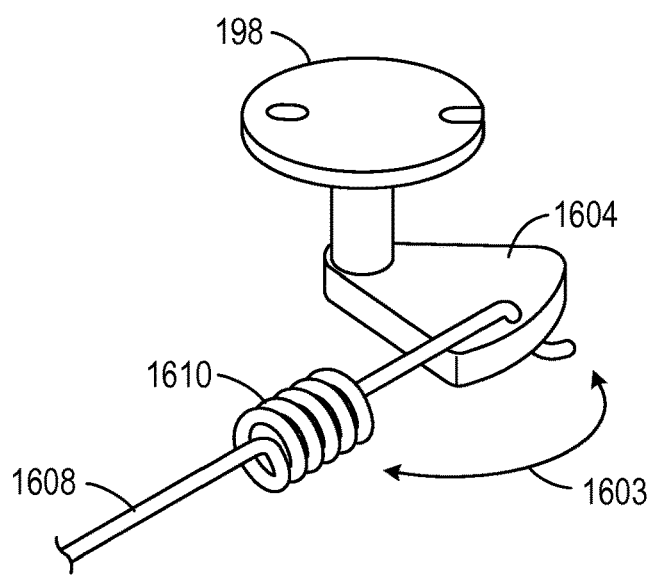
FIG. 24 is a perspective view of an exemplary embodiment of a torque limitation device for an accessory drive device.

Other configurations and geometries for arm 1304 are also possible according to one or more contemplated embodiments. For example, arm 1304 can be configured as a wedge shaped protrusion extending from the shaft 1304 attached to the output disk 198 (e.g., as illustrated in FIG. 24), as an annular flange extending from the shaft 1304 (not shown), or any other shape.

Figure 21A:
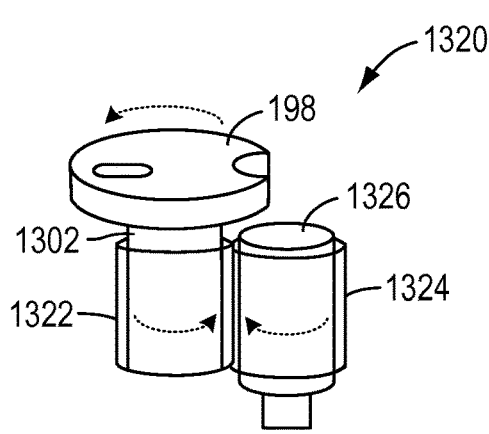
FIG. 21A is a perspective view of an exemplary embodiment of a coupling to a drive disk of the drive mechanism that converts rotational motion of a drive source into rotational motion of the drive disk via a lead screw.

Moreover, one of ordinary skill in the art would further appreciate that other couplings directly interfacing with a shaft of the output disk 198 could also be used to generate a reciprocating rotation of the output disk 198. For example, as illustrated in FIG. 21A, a coupling 1320 can have a lead screw 1326 with threads (shown schematically) 1324 that interface with corresponding threads 1322 on a shaft 1302 of the output disk 198. The lead screw 1326 can be rotated in a reciprocating manner about an axis parallel to an axis of the shaft 1302, which results in a corresponding rotation of the shaft 1302 and thus output disk 198. When the accessory drive includes multiple output disks 198, each output disk 198 may have its own lead screw 1326 so that it can be actuated independently of the other output disks 198. Alternatively, one or more of the output disks 198 may share a lead screw 1326 or have lead screws 1326 otherwise coupled together so that actuation of the output disks 198 is in concert.

Figure 21B:
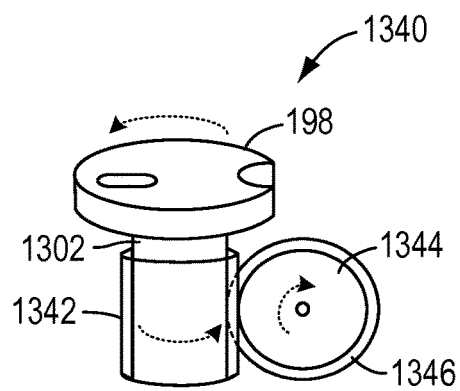
FIG. 21B is a perspective view of another exemplary embodiment of a coupling to a drive disk of the drive mechanism that converts rotational motion of a drive source into rotational motion of the drive disk via a worm wheel.

In another example, as illustrated in FIG. 21B, a coupling 1340 has a worm gear 1346 with splines 1346 (shown schematically) that interface with corresponding splines 1342 on a shaft 1302 of the output disk 198. The worm gear 1346 can be rotated in a reciprocating manner about an axis perpendicular to an axis of the shaft 1302, which results in a corresponding rotation of the shaft 1302 and thus output disk 198. When the accessory drive includes multiple output disks 198, each output disk 198 may have its own worm gear 1346 so that it can be actuated independently of the other output disks 198. Alternatively, one or more of the output disks 198 may share a worm gear 1346 or have worm gears 1346 otherwise coupled together so that actuation of the output disks 198 is in concert.

Figure 22:
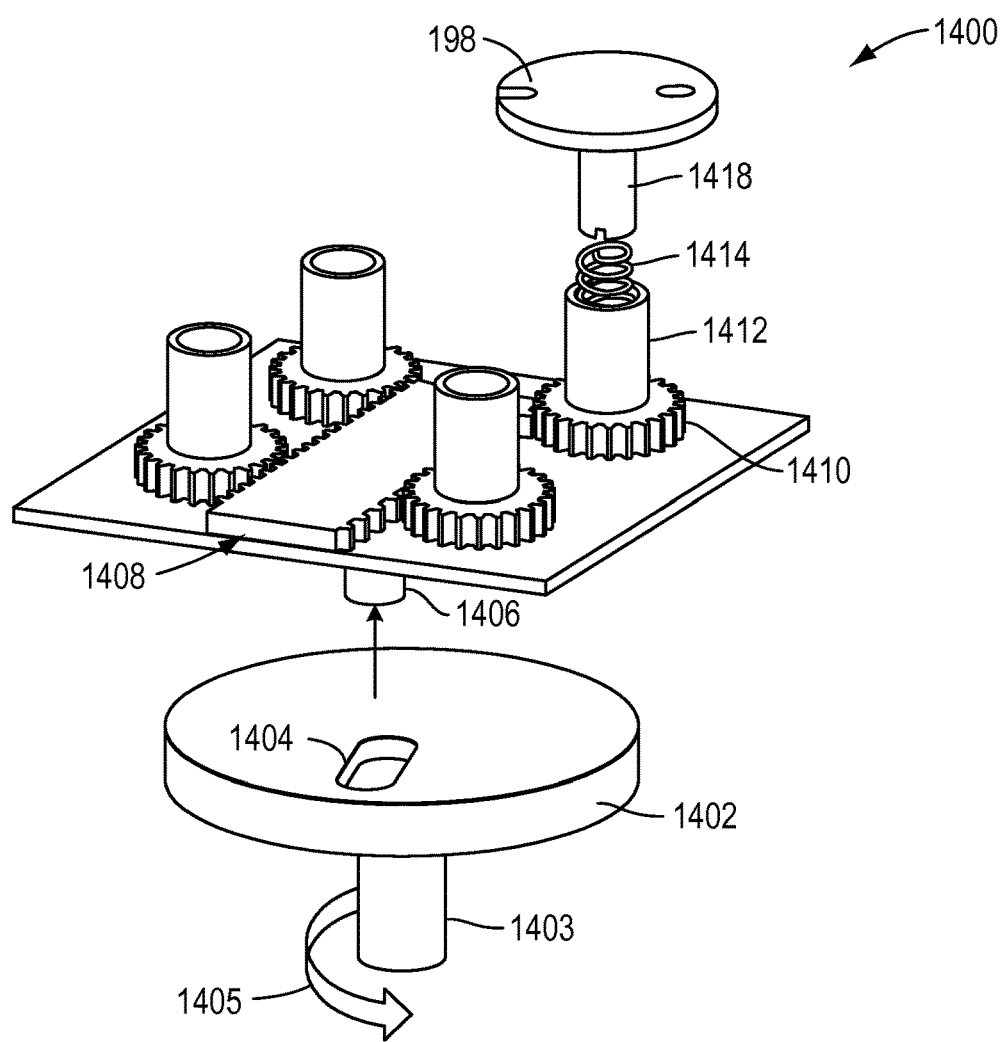
FIG. 22 is a partially exploded perspective view of an exemplary embodiment of a coupling for an accessory drive device that converts rotational motion of a drive source into reciprocating rotational motion.

Drive devices of the various exemplary embodiments described herein may be configured to simultaneously actuate a plurality of output disks of a drive device. As illustrated in FIG. 22, various embodiments of the present disclosure contemplate a coupling 1400 that imparts a reciprocating rotation to a plurality of output disks 198 of an accessory drive device, with only one output disk 198 being depicted in the exemplary embodiment of FIG. 22. Coupling 1400 can be used in the accessory drive devices of the various exemplary embodiments described herein, such as accessory drive device 190 of the exemplary embodiment of FIG. 4.

Coupling 1400 comprises a slotted disk 1402, which may be driven by a motor (not shown) or other motive source, such as a hydraulic motive source as has been described. For example, a shaft 1403 connected to slotted disk 1402 may be driven in the direction indicated by arrow 1405 in the exemplary embodiment of FIG. 22. An output shaft of the motor may have a rotational speed in a range of, for example, from about 0.005 RPM to about 20 RPM. In another exemplary embodiment, the output shaft of the motor may have a rotational speed in a range of, for example, about 0.01 RPM to about 10 RPM. According to an exemplary embodiment, slotted disk 1402 may be driven directly by the motor, such as by shaft 1403 being the output shaft of the motor. According to another exemplary embodiment, shaft 1403 may be indirectly coupled to the motor, such as via, for example, a belt, chain, or other device (not shown) familiar to one of ordinary skill in the art. When shaft 1403 is indirectly coupled to the motor, the motor may be indirectly coupled to a plurality of couplings 1400 so that a plurality of instruments may be actuated by the plurality of couplings 1400. In alternative embodiments, a hydraulic motive source and gear box may be used to rotate shaft 1403.

To actuate the plurality of output disks 198, slotted disk 1410 may be coupled to a rack 1408. For example, rack 1408 may comprise a boss 1406 received within a slot 1404 of slotted disk 1410. Thus, when slotted disk 1410 is rotated, such as along direction 1405, rack 1408 is reciprocated back and forth along the directions indicated by arrows 1411 in the exemplary embodiment of FIG. 22. As a result, the rotational movement of slotted disk 1402 is converted to a translational movement of rack 1408.

Rack 1408 may be coupled to a plurality of pinions 1412 of coupling 1400, with pinions 1412 in turn being coupled to the respective output disks 198, such as via torque limitation devices 1414, as will be discussed in further detail below. For example, rack 1408 may be engaged with geared portions 1410 of respective pinions 1412 so that translational movement of rack 1408 is converted to rotational movement of each of pinions 1412 engaged with rack 1408, which in turn causes rotational movement of the plurality of output disks 198. Thus, the plurality of pinions 1412 engaged with rack 1408 may be simultaneously actuated when rack 1408 is driven by slotted disk 1404.

Figure 23:
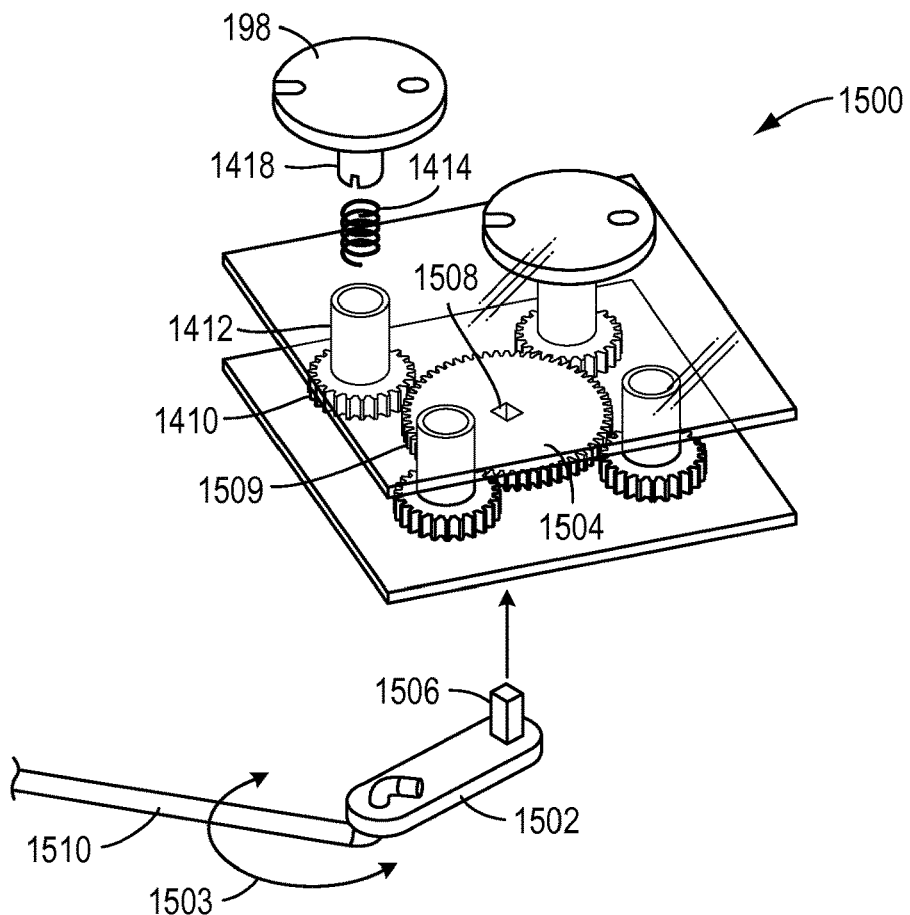
FIG. 23 is a partially exploded perspective view of another exemplary embodiment of a coupling for an accessory drive device that converts rotational motion of a drive source into reciprocating rotational motion.

Other arrangements may be utilized to actuate a plurality of drive disks of a drive device. Turning to FIG. 23, an exemplary embodiment of a coupling 1500 is shown that comprises a drive gear 1504 coupled with a plurality of pinions 1412. For example, teeth 1509 of drive gear 1504 may be engaged with the respective geared portions 1408 of the pinions 1412. Pinions 1412 may in turn be coupled to respective output disks 198 (only one being shown in FIG. 23 for ease of viewing other components of coupling 1500), such as via torque limitation devices 1414, as discussed above with regard to the exemplary embodiment of FIG. 22. Coupling 1500 can be used in the accessory drive devices of the various exemplary embodiments described herein, such as accessory drive device 190 of the exemplary embodiment of FIG. 4.

Drive gear 1504 may be driven in a reciprocating motion to actuate pinions 1412 and the respective output disks 198. According to an exemplary embodiment, a crank 1502 may be coupled to drive gear 1504. For example, a projection 1506 of crank 1502 may be received within hole 1508 of drive gear 1504, with projection 1506 having a cross-sectional shape corresponding to the shape of hole 1508. Crank 1503 may be driven in a reciprocating motion to actuate drive gear 1504 along the directions indicated by arrows 1503 in FIG. 23. For example, a push/pull rod 1510 may be connected to crank 1503, with push/pull rod 1510 being driven in a linear, reciprocating motion by a motor (not shown), causing crank 1502 to pivot about the connection between projection 1506 and hole 1508, which in turn moves crank 1502 along arrows 1503 and reciprocates drive gear 1504 back and forth through an arc. Rod 1510 may be driven via the various drive mechanisms contemplated by the various exemplary embodiments described herein. According to an exemplary embodiment, rod 1510 can be actuated using the exemplary embodiment of FIG. 16 or 17. For example, rod 1510 in the exemplary embodiment of FIG. 23 may be used in place of rod 924 in FIG. 16 or in place of rod 1020 in FIG. 17.

Torque Limitation Mechanisms

As discussed with regard to the various exemplary embodiments herein, actuation of a surgical instrument during a cleaning procedure, such as via actuating a wrist, end effector, or other surgical instrument component (e.g., via a reciprocating motion), may facilitate exposure of various surfaces of the surgical instrument during the cleaning procedure to facilitate cleaning of the surgical instrument. One consideration for actuating surgical instruments in this manner is minimizing or eliminating wear of a surgical instrument, which may have a limited number of cycles of use (e.g., a limited life).

To minimize or eliminate wear of a surgical instrument due to actuation during a cleaning procedure, the accessory drive devices of the various exemplary embodiments described herein may include one or more torque limitation devices that may regulate (e.g., limit) an amount of torque that may be applied to input disks of a surgical instrument.

According to an exemplary embodiment, an output disk 198 of an accessory drive device may be coupled to a crank 1604, as shown in FIG. 24. The exemplary embodiment of FIG. 24 can be used in the accessory drive devices of the various exemplary embodiments described herein, such as accessory drive device 190 of the exemplary embodiment of FIG. 4. Crank 1604 may reciprocate along arrows 1603, such as in a similar manner as crank 1502 of the exemplary embodiment of FIG. 23. For example, crank 1604 may be driven by a push/pull rod 1608 shown in the exemplary embodiment of FIG. 24. According to an exemplary embodiment, push/pull rod 1608 may comprise a torque limitation device 1610 to limit the amount of torque applied to output disk 198. Torque limitation device 1610 may be, for example, a spring that is compliant. Thus, when a component of a surgical device (e.g., an end effector) has been actuated (e.g., opened or closed) to its maximum range of motion, the component may resist further movement, which in turn causes a respective output disk 198 and crank 1604 to resist movement. When this occurs but push/pull rod 1608 is still being actuated, such as via a motor (not shown), to drive crank 1603 and output disk 198, torque limitation device 1610 may minimize or prevent additional force being applied to crank 1603, output disk 198, and the surgical instrument. For instance, the spring forming the torque limitation device 1610 may deform when the surgical instrument, output disk 198, and crank 1604 resist further movement so that an excessive force is not applied to the instrument. In this way, wear of the instrument may be minimized or avoided.

Figure 25:
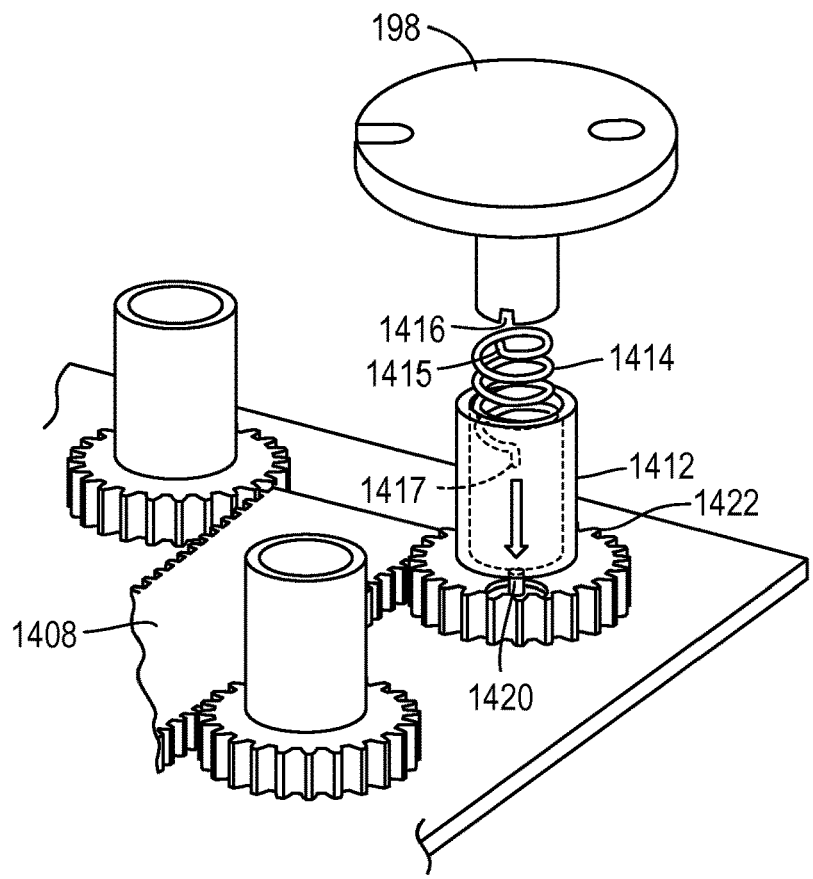
FIG. 25 is a partially exploded, detailed perspective view of an exemplary embodiment of a drive disk for an accessory drive device, the drive disk including a torque limitation device.

As discussed above with regard to the exemplary embodiment of FIG. 24, a device (e.g., push/pull rod 1608) used to actuate an output disk 198 may include a torque limitation device so the torque applied to the output disk 198 is limited. For example, torque limitation devices may be provided for individual drive disks of an accessory drive device. Turning to FIG. 25, an exemplary embodiment of an output disk 198 is shown that is coupled to a torque limitation device 1414. The exemplary embodiment of FIG. 25 may be used in the various exemplary embodiments described herein, such as, for example, in the exemplary embodiment of FIGS. 22 and 23.

Torque limitation device 1414 may be coupled to both output disk 198 and pinion 1412. According to an exemplary embodiment, torque limitation device 1414 can be disposed within a cavity 1422 of pinion 1412 and a first end 1417 of torque limitation device 1414 can be coupled to pinion 1412, such as by receiving first end 1417 of torque limitation device 1414 within an aperture 1420 provided in pinion 1412. A second end 1415 of torque limitation device 1414 may be coupled to output disk 198, such as by receiving second end 1415 within a notch 1416 of output disk 198. As rack 1408 is actuated, rack 1408 actuates and rotates pinion 1412, as described above with regard to the exemplary embodiment of FIG. 22. As pinion 1412 rotates, torque limitation device 1414 rotates as well because torque limitation device 1414 is coupled with pinion 1412 via insertion into aperture 1420. Output disk 198 also is rotated due to the coupling of torque limitation device 1414 with output disk 198. Thus, rotational motion induced in pinion 1412 may be transferred to output disk 198 via torque limitation device 1414. According to an exemplary embodiment, torque limitation device 1414 can be a compliant member. For example, torque limitation device 1414 may be a torsion spring. Due to its compliant nature, torque limitation device 1414 may preferentially deform when a force transmitted from pinion 1412 is excessive, so that the amount of force applied to output disk 198 and any input disk (e.g., input disk 158 of surgical instrument 140 of the exemplary embodiment of FIG. 4) coupled to output disk 198 is limited. As a result, torque limitation device 1414 may function to minimize or prevent excessive force being applied to the input disk of a surgical instrument, which facilitates minimizing wear of the surgical instrument during a cleaning procedure due to actuation of the surgical instrument.

Figures 26A, 26B:
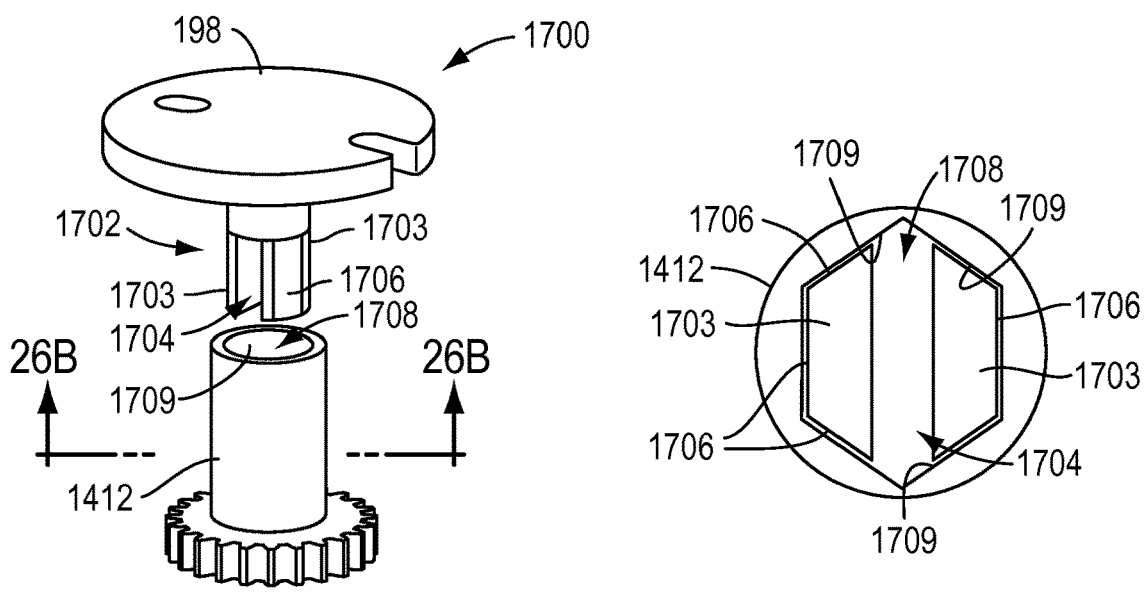
FIG. 26A is an exploded perspective view of an exemplary embodiment of a pinion and a drive disk with coupling surfaces that include a torque limitation feature.
FIG. 26B is a cross-sectional view illustrating the coupling surfaces of the assembled drive disk and pinion along line 26B-26B of FIG. 26A.

The various exemplary embodiments described herein contemplate other configurations in which torque limitation devices are provided for output disks of an accessory drive device to actuate a surgical instrument. According to an exemplary embodiment, an output disk 198 and pinion 1412 of an accessory drive device may comprise a clutch feature, as shown in FIG. 26A. For instance, surfaces of output disk 198 and pinion 1412 may define a clutch feature. As shown in the exemplary embodiment of FIGS. 26A and 26B, a shaft 1702 of output disk 198 may include an arrangement of surfaces 1706 that engage with surfaces of pinion 1412 so that a controlled amount of friction is provided between output disk 198 and pinion 1412. For example, shaft 1702 may be received within a cavity 1708 of pinion 1412, with walls 1709 of cavity 1708 defining surfaces corresponding in shape to surfaces 1706 of output disk 198. According to an exemplary embodiment, surfaces 1706 of output disk 198 and internal walls 1709 of pinion 1412 may be flat. Further, surfaces 1706 of output disk 198 and walls 1709 of pinion 1412 may each comprise, for example, about six flat surfaces to about ten flat surfaces.

As pinion 1412 rotates, such as according to the various exemplary embodiments described herein, output disk 198 also rotates, due to output disk 198 being coupled to pinion 1412 via the engagement of surfaces 1706 of output disk 198 with walls 1709 of pinion 1412. However, should the torque applied from pinion 1412 to output disk 198 become too great, the friction between surfaces 1706 of output disk 198 and wall 1709 of pinion 1412 will be overcome, permitting output disk 198 to slip as pinion 1412 rotates. As a result, the clutch feature of output disk 198 and pinion 1412 may act as a torque limitation feature minimize or prevent excessive force being applied to the input disk of a surgical instrument, thus minimizing wear of the surgical instrument during a cleaning procedure. According to an exemplary embodiment, at least one of output disk 198 and pinion 1412 may include a feature to facilitate slip of output disk 198 relative to pinion 1412. For example, output disk 198 may be structured to deform and facilitate slipping of surfaces 1706 of output disk 198 relative to wall 1709 of pinion 1412. As shown in the exemplary embodiment of FIGS. 26A and 26B, shaft 1702 of output disk 198 may include one or more slots 1704 to facilitate shaft portions 1703 to deform and thus slip relative to pinion 1412. For example, shaft portions 1703 may deform by moving towards one another and away from wall 1709 of pinion 1412 to facilitate slip of shaft 1702 relative to pinion 1412.

Other clutch features used as torque limitation mechanisms may be contemplated by the various exemplary embodiments described herein. As shown in the exemplary embodiment of FIG. 27, the surface 1802 of output disk 198 configured to engage with an input disk (not shown in FIG. 27) of a surgical instrument (e.g., input disk 158 of surgical instrument 140 of the exemplary embodiment of FIG. 4) may be configured to permit slip between output disk 198 and the input disk. For instance, surface 1802 may include grooves 1805 to provide a controlled amount of friction between output disk 198 and an input disk of a surgical instrument. As a result, surface 1802 may act as a clutch feature that limits the amount of torque transmitted from output disk 198 to the input disk when output disk 198 is driven, for example, by a pinion 1412.

Figure 27:
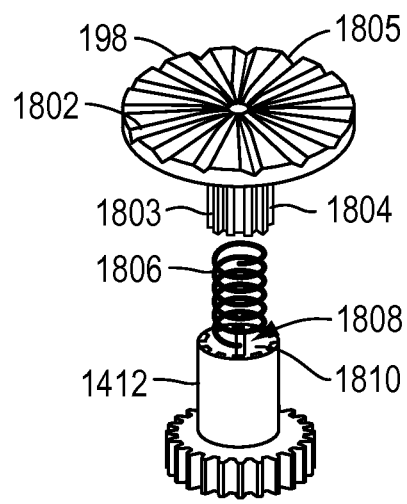
FIG. 27 is an exploded perspective view of an exemplary embodiment of a pinion and a drive disk with a torque limitation feature.

According to an exemplary embodiment, output disk 198 may be coupled with pinion 1412. For example, a shaft 1803 of output disk 198 may have surfaces with shapes corresponding in shape to surfaces of pinion 1412. For instance, shaft 1803 may have a spline shape 1804 and a cavity 1808 of pinion 1412 may have a corresponding spline shape 1810 so that shaft 1803 may be received within cavity 1808, and pinion 1412 and output disk 198 may be coupled to one another. Thus, when pinion 1412 is driven and rotated, such as according to the various exemplary embodiments described herein, output disk 198 also is rotated. However, due to the configuration of surface 1802 of output disk 198, the amount of friction between output disk 198 and the input disk of a surgical instrument is limited, so that when the torque between output disk 198 and the input disk is too great, output disk 198 may slip relative to the input disk. According to an exemplary embodiment, an accessory drive device (e.g., accessory drive device 190 of the various exemplary embodiments described herein) may further include a device to facilitate engagement between output disk 198 and an input disk of a surgical instrument but permit slip between output disk 198 and the input disk. As shown in FIG. 27, a spring 1806 may be disposed within cavity 1808 of pinion 1412 to bias output disk 198 toward an input disk of an instrument and facilitate engagement of output disk surface 1802 with the input disk. Due to the compliant nature of spring 1806, when the torque transmitted to output disk 198 is too great, spring 1806 may deform and permit output disk 198 to move relative to the input disk of a surgical instrument, such as along the direction indicated by arrow 1807 in the exemplary embodiment of FIG. 27, and facilitate slip between output disk surface 1802 and the input disk.

Instrument Coupling and Recognition

As discussed with regard to the various exemplary embodiments herein, because components of a surgical instrument (e.g., wrist or end effector) may have a limited range of motion, it may be desirable to limit the amount of torque transmitted to input disks of a surgical instrument, such as when actuating one or more components of the surgical instrument during a cleaning procedure. An additional consideration is that when a surgical instrument is coupled to an accessory drive device (e.g., accessory drive device 190 of the exemplary embodiment of FIG. 4), a component of the surgical instrument having a limited range of motion (e.g., wrist or end effector) may not be in its neutral position. Instead, the component may already be positioned so the component has been actuated in one direction towards its maximum range of motion. A drive device may actuate the surgical instrument component without regard to this positioning of the surgical instrument component. For instance, the component of the instrument may be actuated by a normal amount of motion to reach its maximum range of motion, causing the component to quickly attain its maximum range of motion, which could cause a high torque to be applied to the instrument, such as when torque limitation features of the various exemplary embodiments described herein are not utilized. In view of this, it may be desirable to actuate surgical instruments in a manner that accommodates a limited range of motion of a surgical instrument component. Further, it may be desirable to provide an accessory drive device with a feature to recognize an instrument so the accessory drive device may use settings appropriate for the particular instrument.

Figure 28:
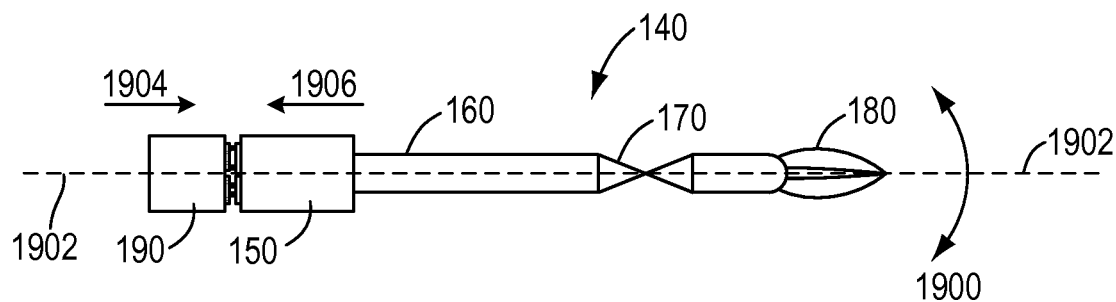
FIG. 28 is a schematic diagram illustrating initial coupling of the accessory drive device of a surgical instrument to a drive mechanism according to one or more exemplary embodiments.

According to an exemplary embodiment, a surgical instrument 140 may be prepared for coupling to an accessory drive device 190, as described above with regard to the exemplary embodiment of FIGS. 3 and 4 and as shown in FIG. 28. Prior to coupling surgical instrument 140 and accessory drive device 190, one or more components of surgical instrument 140 may be moved to a neutral position (e.g., zero position) of the component. For example, a wrist 170 of surgical instrument 140 may be actuated so that wrist 170 and end effector 180 are positioned substantially along a longitudinal axis 1902 of surgical instrument 140, as shown in the exemplary embodiment of FIG. 28. The positioning of wrist 170 and end effector 180 along longitudinal axis 1902 need not be precisely along axis 1902 but approximately along axis 1902. For example, wrist 170 and end effector 180 may be positioned approximately along longitudinal axis 1902 so that actuation of wrist 170 to its maximum range of motion, relative to its neutral position, results in minimal over-torquing of wrist 170. End effector 180 may also be closed, as shown in the exemplary embodiment of FIG. 28. Actuation of wrist 170 may be performed, for example, manually, such as by a technician moving wrist 170 and/or end effector 180 by hand. By moving one or more components of surgical instrument 140 to a neutral position, the components may be driven by accessory drive device 190 in an amount corresponding to a maximum range of motion of the components, thus minimizing over-torquing surgical instrument 140.

Figure 29:
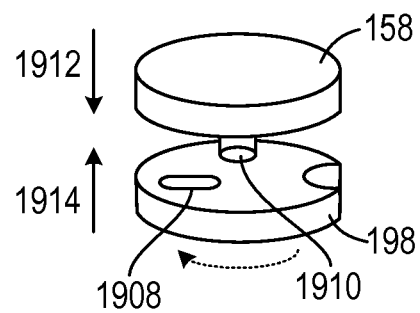
FIG. 29 is an isolated perspective view illustrating the initial coupling between an output disk of an accessory drive device of the surgical instrument and the input disk of a surgical instrument according to one or more embodiments.

Once one or more components of surgical instrument 140 have been moved to a neutral position, surgical instrument 140 may be coupled to accessory drive device 190, such as by moving one or more of surgical instrument 140 and accessory drive device 190 along the directions indicated by arrows 1904 and 1906 in the exemplary embodiment of FIG. 28. When this occurs, the output disks of accessory drive device 190 and the input disks of transmission mechanism 150 (e.g., output disks 198 of accessory drive device 190 and input disks 158 of the exemplary embodiment of FIG. 4) may be in loose contact so that the output disks and the input disks are not coupled to one another. The output disks of accessory drive device 190 may be driven and rotated relative to input disks of surgical instrument 140 until the output disks and input disks couple to one another. As shown in the exemplary embodiment of FIG. 29, an output disk 198 of accessory drive device 190 may be rotated relative to an input disk 158 of surgical instrument 140 until a recess 1908 of output disk 198 is aligned with a boss 1910 of input disk 158, resulting in boss 1910 being received within recess 1908 (e.g., due to loose pressing of drive disk 198 against input disk 158 along the directions of arrows 1912 and 1914 in FIG. 29) to couple output disk 198 and input disk 158. Although the exemplary embodiment of FIG. 29 depicts boss 1910 being located on input disk 158 and recess 1908 on output disk 198, the positions of boss 1910 and recess 1908 may be reversed in other exemplary embodiments.

According to an exemplary embodiment, coupling of accessory drive device 190 with surgical instrument 140 may be detected to indicate that one or more components of surgical instrument (e.g., wrist 170 and/or end effector 180) are substantially positioned at a neutral position. As a result, accessory drive device 190 may actuate one or more components of surgical instrument 140 according to a maximum range of motion of the one or more components, relative to the neutral position of the one or more components, so that over-torquing of surgical instrument 140 is minimized or avoided.

Figure 30:
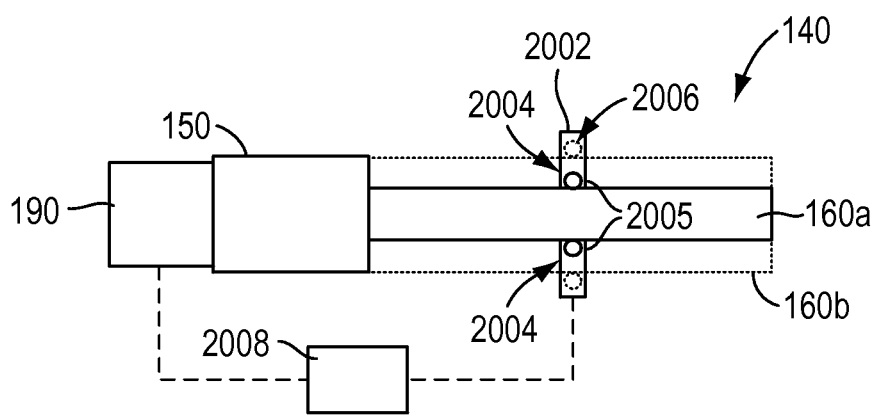
FIG. 30 is a diagrammatic view illustrating an exemplary embodiment of a surgical instrument recognition device.

According to an exemplary embodiment, a brief increase in torque may be detected by accessory drive device 190 when output disk 198 and input disk 158 are coupled to one another. For example, a brief increase in torque for output disk 198 may be detected by accessory drive device 190 when output disk 198 and input disk 158 couple to one another. According to an exemplary embodiment, accessory drive device 190 may include a sensor to detect torque of an output disk 198, such as, for example, a strain gauge, a reed switch and magnet used in conjunction with a spring, or other torque sensors familiar to one skilled in the art. In another example, a brief increase in torque may be detected by accessory drive device 190 when motion of wrist 170 and/or end effector 180 is constrained, such as via manual constraint by a technician or a sleeve (not shown) temporarily placed about surgical instrument 140, and input disk 158 is briefly driven by output disk 198. In another example, motor current, such as for a motor driving accessory drive device 190, may be monitored to detect an increase in amperage as end effectors (not shown in FIG. 30) of instrument contact a restraint, such as, for example, a manual constraint by a technician (e.g., by hand) or a sleeve (not shown) temporarily placed about surgical instrument 140.

According to another exemplary embodiment, coupling of output disk 198 and input disk 158 may be detected by a technician and reported to accessory drive device 190. For example, when output disk 198 and input disk 158 become coupled to one another, as discussed above with regard to the exemplary embodiment of FIG. 29, a technician may hear a click sound. The technician may provide an input to accessory drive device 190 indicating that output disk 198 and input disk 158 are coupled, which further indicates that one or more components of surgical instrument 140 are at a neutral position due to positioning of the components, as discussed above with regard to the exemplary embodiment of FIG. 28. According to another exemplary embodiment, coupling of output disk 198 and input disk 158 may be determined by detecting that output disk 198 has moved towards input disk 158, such as along the direction indicated by arrows 1912 and 1914 in FIG. 29. This indicates, for example, that boss 1910 has been received within recess 1908.

According to an exemplary embodiment, accessory drive devices 190 of the various exemplary embodiments described herein may be configured to avoid over-torquing a surgical instrument 140, such as due to the limited range of motion of one or more components of the surgical instrument 140. For example, an accessory drive device 190 may include one or more torque limitation devices, as described above with regard to the exemplary embodiments of FIGS. 24-27. With regard to the exemplary embodiments of FIGS. 24 and 25, springs 1610 and 1414 may be highly compliant springs so that when a maximum range of motion for a surgical instrument component (e.g., wrist 170 or end effector 180) is achieved, springs 1610 and 1414 may deform and minimize over-torquing of surgical instrument 140. According to an exemplary embodiment, springs 1610 and 1414 may deform when a surgical instrument component is actuated in more than one direction (e.g., when end effector 180 is opened or closed).

Surgical instruments may vary, such as in size, shape, or other parameters, and use varying parameters for actuation. In view of this, accessory drive devices of the various exemplary embodiments described herein contemplate the ability to recognize what type of instrument is coupled to the accessory drive device. As a result, the accessory drive device may actuate a surgical instrument, such as during a cleaning procedure, according to predetermined actuation parameters stored in a non-volatile memory (e.g., flash memory, magnetic memory, optical disc, and other types of non-volatile memory familiar to one of ordinary skill in the art) to achieve actuation of the surgical instrument while minimizing over-torquing the instrument.

According to an exemplary embodiment, accessory drive devices 190 of the various exemplary embodiments described herein may include a device for a user to select the type of surgical instrument being coupled to an accessory drive device 190. For example, an accessory drive device 190 may comprise a manual dial selector, a manual switch, a graphical user input, or a sensor to automatically detect the type of instrument. According to an exemplary embodiment, a sensor to detect the type of instrument may be configured to detect structures on surgical instrument 140, such as one or more protrusions or other features on force transmission mechanism 150. According to another exemplary embodiment, a sensor to detect the type of instrument may be configured to detect a device including identification information for an instrument, such as, for example, a bar code, quick code, a chip in surgical instrument 140 (e.g., RFID chip), with the chip including identification information about the instrument that is read by the sensor.

According to an exemplary embodiment, an accessory drive device 190 may include a device that automatically detects a size of a surgical instrument 140. A size of a surgical instrument, such as a width of a shaft 160 of a surgical instrument 140, may be utilized to select actuation parameters for the instrument because actuation parameters may vary with size of surgical instruments. For instance, an instrument having a shaft with a large diameter may use less torque than an instrument having a shaft with a smaller diameter. As shown in the exemplary embodiment of FIG. 30, an instrument width sensor 2002 may be connected to an accessory drive device 190, such as via a controller 2008. Sensor 2002 may be configured to automatically detect a size (e.g. diameter) of a shaft of a surgical instrument, such as, for example, whether surgical instrument 140 has a shaft 160a with a small diameter or a shaft 160b (shown with dashed lines in FIG. 30) with a larger diameter. According to an exemplary embodiment, sensor 2002 may include members 2004 (e.g., pins or other type of member) configured to contact an outer surface of the shaft. For example, members 2004 may be displaceable, such as between a first position 2005 and a second position 2006 in FIG. 30, so that members 2004 may be biased against an outer surface of an instrument shaft. As a result, sensor 2002 may determine a size of shaft, such as, for example, by determining a distance between members 2004 on opposite sides of an instrument shaft. According to an exemplary embodiment, sensor 2002 may output a signal to controller 2008 indicating a size of instrument shaft. Controller 2008 may in turn control accessory drive device 190 according to parameters (e.g., torque) appropriate for the detected shaft size, according to an exemplary embodiment. For example, controller 2008 may control accessory drive device 190 according to predetermined actuation parameters stored in a non-volatile memory (not shown) (e.g., flash memory, magnetic memory, optical disc, and other types of non-volatile memory familiar to one of ordinary skill in the art) included in controller 2008 or connected to controller 2008.

Devices to Facilitate Engagement Between Output and Input Disks

As discussed above with regard to the exemplary embodiment of FIG. 27, an output disk 198 of an accessory drive device 190 may include a device to facilitate engagement between output disk 198 and an input disk of a surgical instrument (e.g., input disk 158 of the exemplary embodiment of FIG. 4). The various exemplary embodiments described herein may include a feature to facilitate engagement between an output disk and an input disk. Such features may minimize slip between the output disk and input disk within a normal range of torque while minimizing wear or other damage that could occur if the output disk and input disk were otherwise coupled via a rigid connection.

Figure 31:
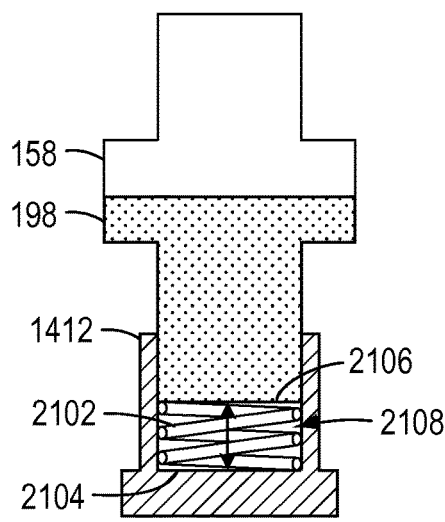
FIG. 31 is a cross-sectional view of an exemplary embodiment of an output disk of an accessory drive device coupled to an input disk of a surgical instrument.

An output disk 198 of an accessory drive device 190 may be biased against an input disk 158 via a spring 2102 placed within a cavity 2108 of pinion 1412, as shown in the exemplary embodiment of FIG. 31. Spring 2102 may contact a surface 2104 of pinion 1412 and a bottom surface 2106 of output disk 198 to urge the output disk 198 against input disk 158 and facilitate contact between output disk 198 and input disk 158. Spring 2102 may be, for example, a helical compression spring or other type of spring familiar to one of ordinary skill in the art. For example, spring may instead be a flat spring 2103 or a wire form spring 2105, as shown in the exemplary embodiments of FIGS. 32A and 32B.

Figure 33:
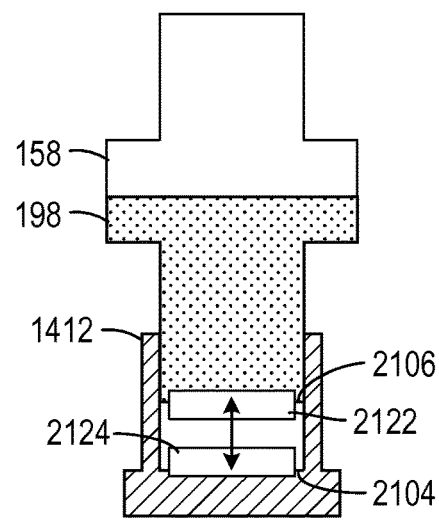
FIG. 33 is a cross-sectional view of another exemplary embodiment of an output disk of an accessory drive device coupled to an input disk of a surgical instrument.
Figure 32A:
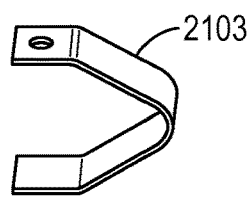
FIG. 32A is a perspective view of an exemplary embodiment of a flat spring that can be used in the embodiment of FIG. 31.
Figure 32B:
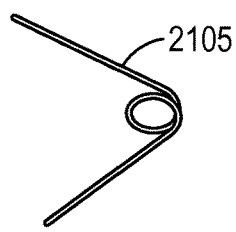
FIG. 32B is a perspective view of an exemplary embodiment of a wire form spring that can be used in the embodiment of FIG. 31.
Figure 34:
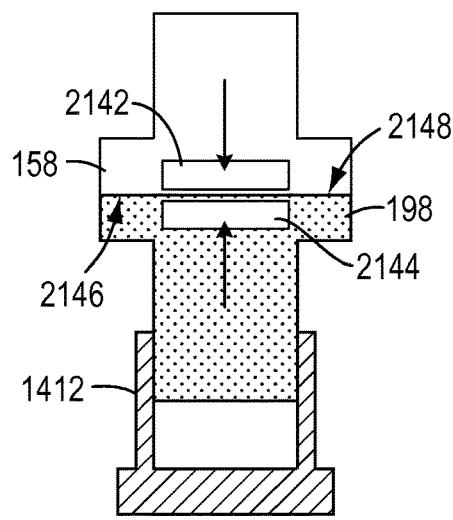
FIG. 34 is a cross-sectional view of another exemplary embodiment of an output disk of an accessory drive device coupled to an input disk of a surgical instrument, with the accessory drive device including a device to facilitate contact between the output disk and input disk.
Figure 35:
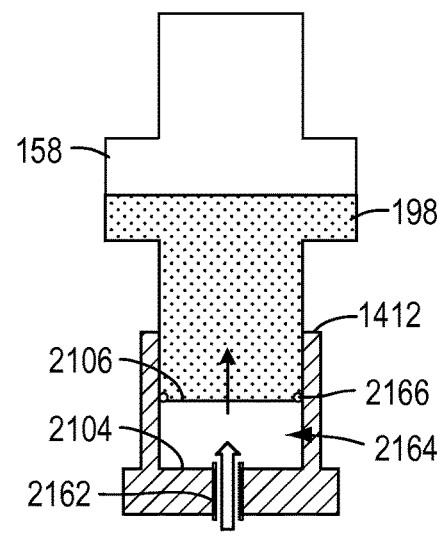
FIG. 35 is a cross-sectional view of another exemplary embodiment of an output disk of an accessory drive device coupled to an input disk of a surgical instrument.

Devices to facilitate contact between output and input disks are not limited to the exemplary embodiments of FIGS. 31, 32A, and 32B. As shown in the exemplary embodiment of FIG. 33, magnets 2124 and 2122 may be provided within pinion 2124 and output disk 198. For example, a first magnet 2124 may be disposed in surface 2104 of pinion 1412 and a second magnet 2122 may be disposed in surface 2106 of output disk 198. Magnets 2124 and 2122 may have the same polarity so that magnets 2124 and 2122 repulse one another and urge output disk 198 against input disk 158. According to another exemplary embodiment, magnets 2142 and 2144 respectively provided within input disk 158 and output disk 198 may have differing polarities, as shown in FIG. 34. For instance, a first magnet 2144 may be disposed within a surface 2146 of output disk 198 and a second magnet 2142 may be disposed within a surface 2148 of input disk 158. As a result, output disk 198 may be urged against input disk 158 due to the attraction between magnets 2142 and 2144. Further, other devices than magnets and springs may be used to facilitate contact between input and output disks. As shown in the exemplary embodiment of FIG. 35, pinion 1412 may include a passage 2162 to receive fluid (e.g., hydraulic fluid or other fluid) within a cavity 2164 of pinion 1412. The pressure of the fluid received within cavity 2164 may press against surface 2106 of output disk 198 and urge output disk 198 against input disk 158, as shown in FIG. 35. Output disk 198 may include a sealing feature 2166, such as, for example, a compliant O-ring, to facilitate fluidic sealing of cavity 2164.

Other Reprocessing Tools

The various exemplary embodiments described herein further contemplate brush devices to facilitate cleaning and reprocessing of surgical instruments. As shown in the exemplary embodiment of FIG. 36A, at least a portion of a surgical instrument 140 may be inserted within one or more brush devices 2202. Brush device 2202 may include, for example, bristles 2204 that define a channel 2208 through which at least a portion of surgical instrument 140 (e.g., end effector 180, wrist 170, and/or a portion of shaft 160) is inserted, such as along a longitudinal axis 1902 of brush device 2202. According to an exemplary embodiment, brush device 2202 may be moved by an actuator 2206 to produce relative movement between bristles 2204 and instrument 140. Actuator 2206 can be, for example, a hydraulic piston, a drive mechanism of the various exemplary embodiments described herein (e.g., drive mechanisms 200, 300, 400, 500, 600, 900, 1000 of FIGS. 5-11, 16, 17), or other actuator familiar to one of ordinary skill in the art. For example, actuator 2206 may rotate brush device 2202, such as about axis 1902 in the direction indicated by arrow 2203 in the exemplary embodiment of FIG. 36B. In another exemplary embodiment, actuator 2206 may move brush device 2202 linearly, such as along axis 1902 in the direction indicated by arrow 2205 in FIG. 36A. In another exemplary embodiment, brush device 2202 may be either rotated along arrow 2203 or translated along arrow 2205, or brush device 2202 may be both rotated and translated along respective arrows 2203 and 2205. According to an exemplary embodiment, brush device 2202 may be actuated, for example, via fluid from a sink, fluid from a reprocessing device, or other motive forces familiar to one of ordinary skill in the art.

According to an exemplary embodiment, transmission mechanism 150 of surgical instrument 140 may be coupled with an accessory drive device (not shown, e.g., accessory drive device 190 of the exemplary embodiment of FIG. 4) to actuate surgical instrument 140. According to an exemplary embodiment, surgical instrument 140 and actuator 2206 may be controlled in a manner so that instrument 140 is not actuated when instrument 140 is brushed, such as to minimize catching bristles 2204 of brush as components of instrument 140 are actuated.

Figure 36A:
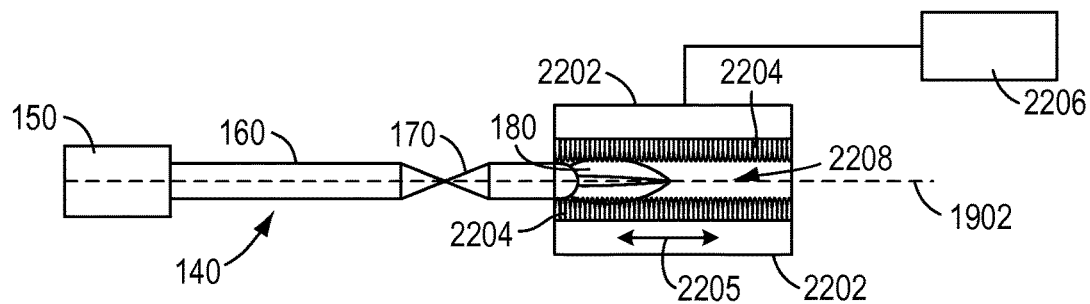
FIG. 36A is a schematic diagrammatic view of an exemplary embodiment of a reprocessing device employing one or more brush devices.
Figure 36B:
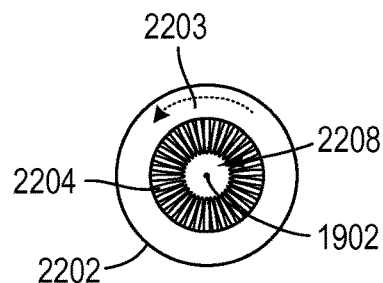
FIG. 36B is an end view of the brush device of FIG. 36A.
Figure 37A:
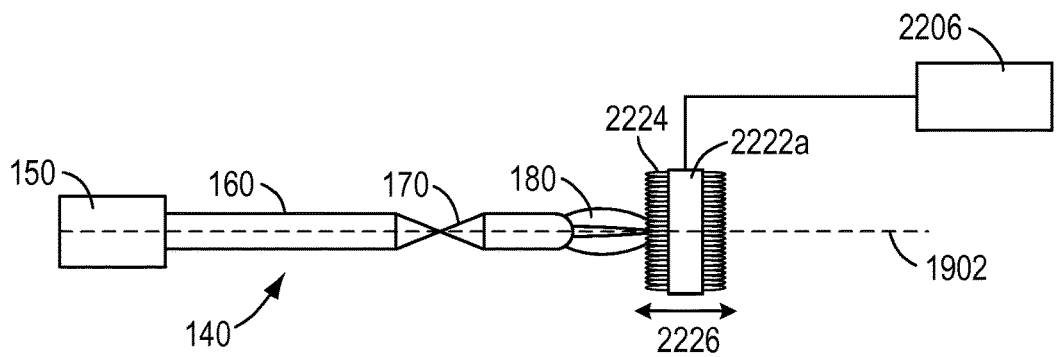
FIG. 37A is a diagrammatic view of another exemplary embodiment of a reprocessing device employing one or more brush devices.
Figure 37B:
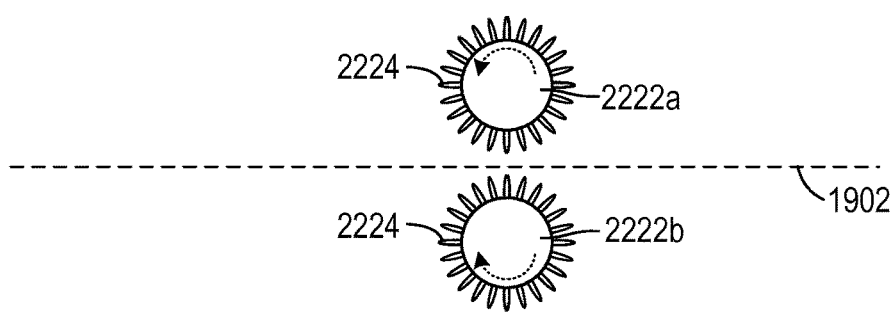
FIG. 37B is an end view of the brush devices of FIG. 37B.

Other brush device arrangements are contemplated than those depicted in the exemplary embodiment of FIGS. 36A and 36B. According to an exemplary embodiment, at least a portion of a surgical instrument 140 may be inserted between brush devices 2222a and 2222b, as shown in FIGS. 37A and 37B. For example, surgical instrument 140 may be translated along the directions indicated by arrows 2226 in FIG. 37A, such as along axis 1902. Brush devices 2222a, 2222b may include bristles 2224 and be rotated, such as via actuator 2206, as shown in FIG. 37B to urge bristles 2224 against instrument 140 and facilitate cleaning of instrument 140.

Various exemplary embodiments and methods described herein have been described as being utilized with surgical instruments for teleoperated surgical systems. However, the exemplary embodiments and methods described herein may be used with other minimally invasive, remotely controlled surgical devices, such as laparoscopic instruments and other manual, hand held instruments, with appropriate modifications made to the accessory drive devices to couple to the transmission mechanisms associated with such manually operated instruments.

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are non-limiting, and modifications to structure, dimensions, materials, and methodologies may be made without departing from the scope of the present teachings.

Other embodiments in accordance with the present disclosure will be apparent to those skilled in the art from consideration of the specification and practice of the invention disclosed herein. It is intended that the specification and examples be considered as exemplary only, with a true scope and spirit being indicated by the following claims being entitled to their full breadth of scope, including equivalents.

What is claimed is:

1. An accessory drive device for surgical instrument reprocessing, comprising:
a housing;
a fluid inlet in flow communication with the housing;
a fluid outlet in flow communication with the housing;
a drive mechanism disposed within the housing; and
an output drive member coupled to and driven by the drive mechanism, the output drive member being configured to engage with an input drive member on a transmission mechanism of the surgical instrument;

wherein the drive mechanism is configured to be driven by fluid flowing through the housing from the inlet to the outlet, the fluid being from a fluid source of a reprocessing device.

2. The device of claim 1, wherein the drive mechanism is configured to be driven by fluid having a pressure at the inlet from about 10 psi to about 60 psi.

3. The device of claim 1, wherein the drive mechanism is configured to be driven by fluid having a flow rate at the inlet of from about 1 L/min to about 60 L/min.

4. The device of claim 1, wherein the drive mechanism is configured to be driven by fluid chosen from at least one of water and a cleaning solution.

5. The device of claim 1, wherein the drive mechanism comprises an impeller and a gear box.

6. The device of claim 1, wherein the drive mechanism comprises a reciprocating piston and a gear box.

7. The device of claim 1, wherein the drive mechanism comprises a pair of bladders and a plate positioned between the bladders.

8. The device of claim 1, wherein the drive mechanism is configured to impart motion to actuate a component of the surgical instrument chosen from a wrist mechanism and an end effector.

9. The device of claim 1, further comprising a torque limitation device configured to limit a torque output by the output drive member.

10. The device of claim 1, further comprising a biasing device configured to urge the output drive member into contact with the input drive member so as to inhibit slip between the output drive member and the input drive member.

* * * * *